United States Patent
Marelli et al.

(10) Patent No.: US 10,791,689 B2
(45) Date of Patent: Oct. 6, 2020

(54) **HYBRID PLANT PRODUCTS FROM *THEOBROMA* SPECIES AND METHODS OF MAKING THE SAME**

(71) Applicant: Mars, Incorporated, McLean, VA (US)

(72) Inventors: Jean-Philippe Marelli, Mogi Mirim (BR); Chigozie V. Nwosu, Hackettstown, NJ (US); Juan Carlos Motamayor Arias, Miami, FL (US); Carolina Schaper Bizzotto, Mogi Mirim (BR); Rodrigo Campos, Elizabethtown, PA (US); Stefan Emiel Royaert, Mogi Mirim (BR)

(73) Assignee: Mars, Incorporated, McLean, VA (US)

( * ) Notice: Subject to any disclaimer, the term of this patent is extended or adjusted under 35 U.S.C. 154(b) by 177 days.

(21) Appl. No.: 15/542,381

(22) PCT Filed: Jan. 11, 2016

(86) PCT No.: PCT/US2016/012911
§ 371 (c)(1),
(2) Date: Jul. 7, 2017

(87) PCT Pub. No.: WO2016/112396
PCT Pub. Date: Jul. 14, 2016

(65) Prior Publication Data
US 2017/0367367 A1    Dec. 28, 2017

Related U.S. Application Data

(60) Provisional application No. 62/101,917, filed on Jan. 9, 2015.

(51) Int. Cl.
| | |
|---|---|
| *A01H 1/02* | (2006.01) |
| *A01H 1/04* | (2006.01) |
| *A01H 5/10* | (2018.01) |
| *A01H 6/60* | (2018.01) |
| *C12Q 1/68* | (2018.01) |
| *C12Q 1/6827* | (2018.01) |
| *C12Q 1/6895* | (2018.01) |

(52) U.S. Cl.
CPC .............. *A01H 1/02* (2013.01); *A01H 1/04* (2013.01); *A01H 5/10* (2013.01); *A01H 6/60* (2018.05); *C12Q 1/6827* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS 4,326,358 A    4/1982    Lawrence et al.

OTHER PUBLICATIONS

Kuhn et al. Evaluating Theobroma grandiflorum for comparative genomic studies with Theobroma cacao. Tree Genetics & Genomes. Oct. 1, 2010, vol. 6, No. 5, pp. 783-792. (Year: 2010).*
Martinson. Hybridization of Cacao and Theobroma grandiflora. Journal of Heredity, vol. 57, Issue 4, Jul. 1966, pp. 134-136. (Year: 1966).*
Kuhn et al. Evaluating Theobroma grandiflorum for comparative genomic studies with Theobroma cacao. Tree Genetics & Genomes (2010) 6:783-792. (Year: 2010).*
Clement et al. Origen and Domestication of Native Amazonian Crops. Diversity 2010, 2, 72-106. (Year: 2010).*
Dand. The International Cocoa Trade, Third Edition, 2011, Woodhead Publishing, Chapter 2—Agronomics of international cocoa production, pp. 23-64. (Year: 2011).*
Hammerstone et al. Purine alkaloid distribution with Herrania and Theobroma. Phytochemistry, vol. 35, No. 5, Mar. 1994, pp. 1237-1240. (Year: 1994).*
Gilabert-Escriva et al. Fatty acid and triacylglycerol composition and thermal behavior of fats from seeds of Brazilian Amazonian *Theobroma* species. Journal of the Science of Food and Agriculture, 82:1425-1431 (2002). (Year: 2002).*
Faleiro et al., "Uso De Marcadores Moleculares Rapd E Microssatelites Visando A Confirmacao Da Fecundacao Cruzada Entre— Theobroma cacao E Theobroma grandiflorum", Agrotropica, vol. 15, No. 1, 2003, pp. 41-46 (English Abstract Submitted).
International Preliminary Report on Patentability received for PCT Patent Application No. PCT/US2016/012911, dated Jul. 20, 2017, 8 pages.
International Search Report and Written Opinion received for PCT Patent Application No. PCT/US2016/012911, dated Mar. 18, 2016, 11 pages.
Office Action received for Australian Patent Application No. 2016205045, dated Jun. 1, 2018, 7 pages.
Posnette, "Interspecific pollination in Theobroma", Tropical Agriculture 22:188-190 (1945).
Adamson, et al., "HPLC method for the Quantification of Procyanidins in Cocoa and Chocolate Samples and Correlation to Total Antioxidant Capacity", J. Agric. Food Chem. 47, 1999, 4184-4188.
Addison, et al., "Hybridization and grafting in species of *Theobromo* which occur in Amazonia", Evolution 6: 380-386 (1952).

(Continued)

*Primary Examiner* — Cynthia E Collins

(57) ABSTRACT

Methods for hybridizing members of the *Theobroma* genus, and particularly to methods for hybridizing *Theobroma cacao* and *Theobroma grandiflorum* are provided. Hybrid seeds, plants and plant parts thereof, obtained from these methods are also provided. Methods for confirming that the resulting progeny are hybrids are described. *Theobroma* hybrid plant products, such as seeds obtained by crossing *Theobroma cacao* and *Theobroma grandiflorum*, having modified chemical compositions, such as modified fatty acid content, and/or modified alkaloid content, are provided. Products obtainable from the hybrid plants and seeds, particularly foodstuffs such as cocoa products, are also provided.

15 Claims, 31 Drawing Sheets

Specification includes a Sequence Listing.

(56) References Cited

OTHER PUBLICATIONS

Ashihara, et al., "Distribution, Biosynthesis and Catabolism of Methylxanthines in Plants", Handb Exp Pharmacol., Aug. 19, 2010, vol. 200, pp. 11-31.
Badings, et al., "Glass Capillary Gas Chromatography of Fatty Acid Methyl Esters. A Study of Conditions for the Quantitative Analysis of Short- and Long-Chain Fatty Acids in Lipids", J. Chromatography, 279, 493-506 (1984).
Blauch, et al., "HPLC Determination of Caffeine and Theobromine in Coffee, Tea and Instant Hot Cocoa Mixes", Journal of Food Science, 48, (1983), pp. 745-747.
Borrone, et al., "Isolation, characterization, and development of WRKY genes as useful genetic markers in Theobroma cacao", Theor. Appl. Genet. 109 (3), 495-507 (2004).
Carpenter, et al., "Lipid Composition of Herrania and Theobroma Seeds", J. Am. Oil Chem. Soc. 71: 845-851 (1994).
Christie, Gas Chromatography and Lipids: A Practical Guide, The Oily Press, Dundee (1989), 191 pp.
Christie, "A Simple Procedure for Rapid Transmethylation of Glycerolipids and Cholesteryl Esters", J. Lipid Res., 23, 1072-1075 (1982).
Cuatrecasas, "Cacao and its allies: a taxonomic revision of the genus *Theobroma*", Contributions from The United States National Herbarium 35: 379-614 (1964).
Gilabert-Escriva, et al., "Fatty acid and triacylglycerol composition and thermal behavior of fats from seeds of Brazilian Amazonian *Theobroma* species", Journal of the Science of Food and Agriculture, 82: 1425-1431 (2002).
Kelm, "High Performance Liquid Chromatography separation and purification of cacao (*Theobroma cacao* L.) procyanidins according to degree of polymerization using a diol stationary phase", J Agric. Food Chem. 54, 2006, 1571-1576.
Kuhn, et al., "Evaluating Theobroma grandiflorum for comparative genomic studies with Theobroma cacao", Tree Genetics & Genomes, 6:783-792 (2010).
Kuhn, et al., "Identification and mapping of conserved ortholog set (COS) II sequences of cacao and their conversion to SNP markers for marker-assisted selection in Theobroma cacao and comparative genomics studies", Tree Genetics & Genomes 8, 97-111 (2012).
Livingstone et al., "Development of single nucleotide polymorphism markers in Theobroma cacao and comparison to simple sequence repeat markers for genotyping of Cameroon clones", Mol Breeding 27:93-106 (2011).
Martinson, "Hybridization of cacao and Theobroma grandiflora", Journal of Heredity, 57:134-136 (1966).
Pugh, et al., "A New Cacao Linkage Map Based on Codominant Markers: Development and Integration of 201 New Microsatellite Markers", Theor. Appl. Genet. 108 (6), 1151-1161 (2004).
Silva, et al., "Description of Amazonian *Theobroma* L. collections, species identification, and characterization of interspecific hybrids", Acta Botanica Brasilis 18:333-341 (2004).

\* cited by examiner

Figure 1

Fatty Acid Composition (%)

| Theobroma Species | Palmitic Acid (C16:0) | Palmitoleic Acid (C16:1) | Stearic Acid (C18:0) | Oleic Acid (C18:1) | Linoleic Acid (C18:2) | Linolenic Acid (C18:3) | Arachidic Acid (C20:0) | Behenic Acid (C22:0) |
|---|---|---|---|---|---|---|---|---|
| T. cacao | 30.6 | 0.6 | 33.9 | 31.4 | 2.5 | trace | 0.9 | trace |
| T. sylvestre | 42.0 | 0.6 | 24.0 | 28.4 | 4.4 | trace | 0.6 | trace |
| T. speciosum | 46.9 | 0.8 | 20.2 | 23.3 | 7.2 | trace | 1.3 | trace |
| T. bicolor | 8.1 | 0.2 | 47.8 | 41.0 | 1.2 | trace | 1.6 | trace |
| T. obovatum | 8.6 | trace | 31.7 | 42.0 | 6.1 | trace | 9.7 | 1.4 |
| T. grandiflorum | 8.5 | 0.2 | 34.6 | 42.0 | 3.4 | trace | 9.9 | 1.3 |
| T. subincanum | 6.8 | 0.4 | 31.8 | 45.6 | 3.2 | 0.7 | 10.3 | 1.4 |
| T. microcarpum | 14.4 | 0.8 | 6.4 | 31.4 | 27.1 | 3.6 | 6.6 | 9.8 |

Figure 3
A
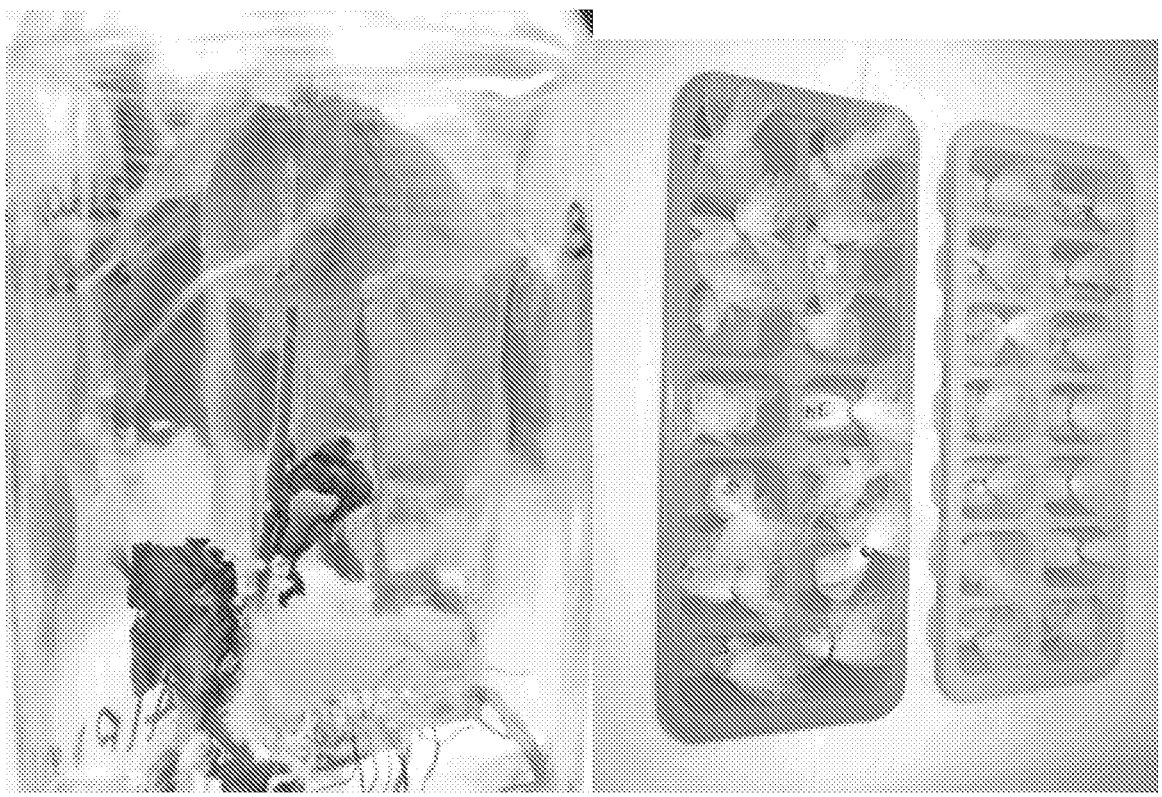
B                                                                 C Figure 4
A
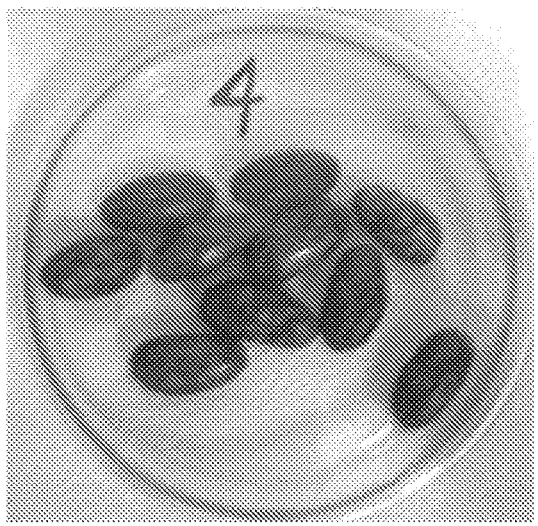
B
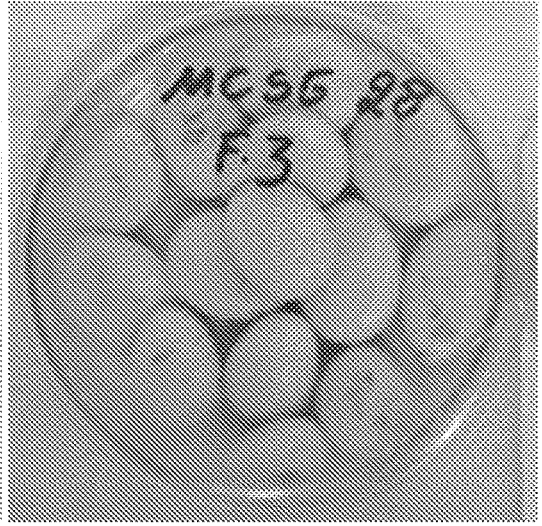
C
D
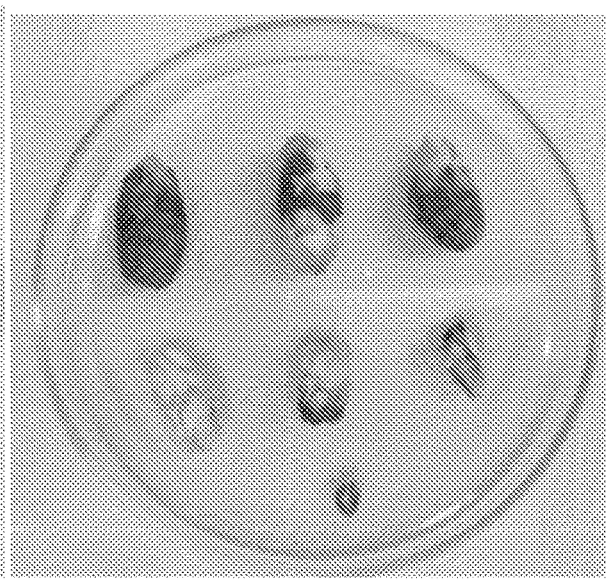

Figure 5
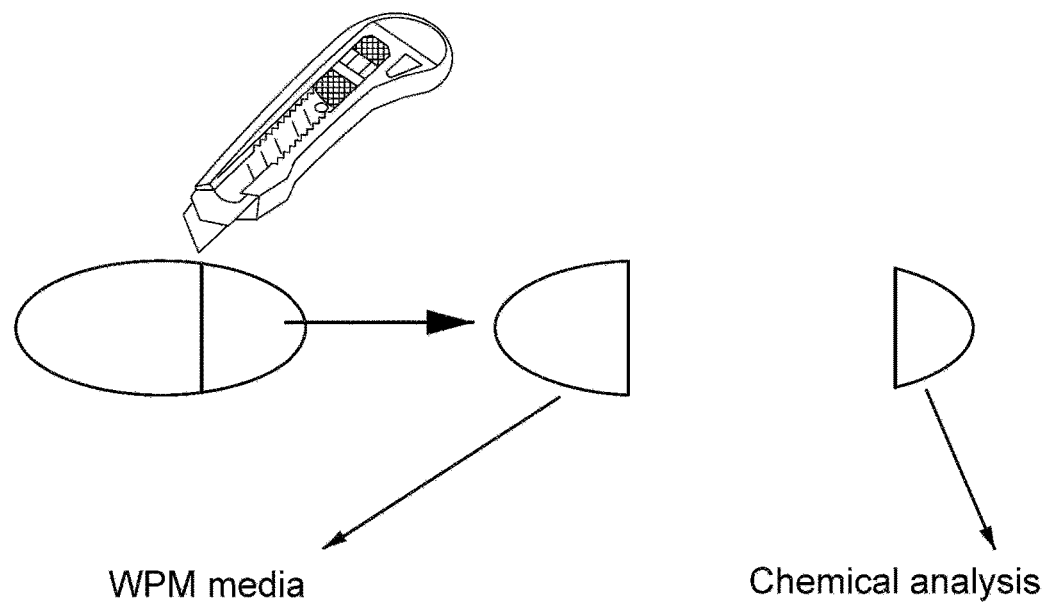
WPM media             Chemical analysis
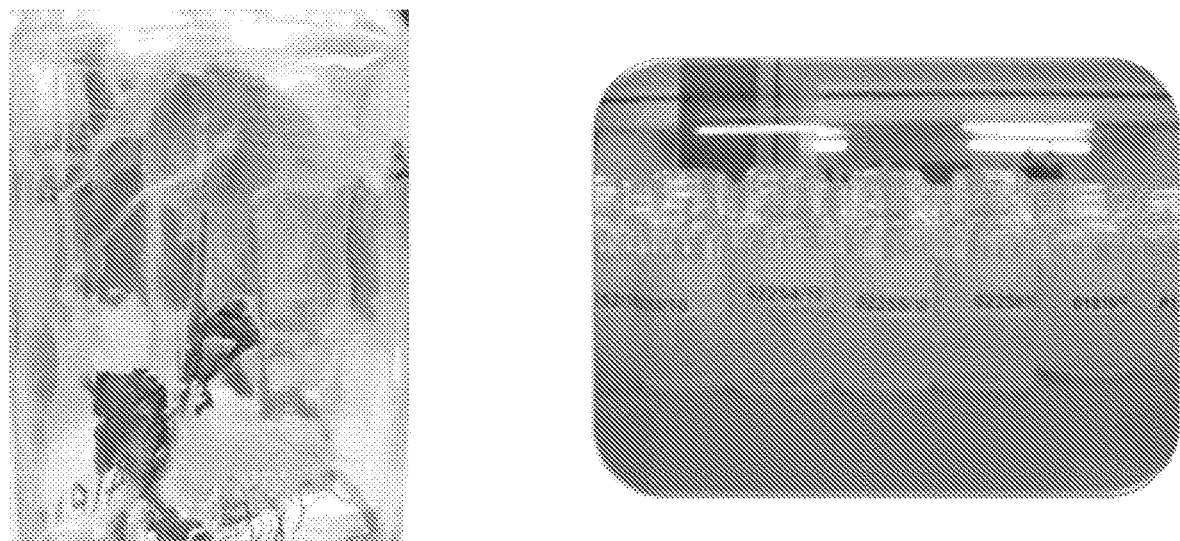

Figure 8
A
B

Figure 9

| Cross | Length | Median | Mean | Sd | P.value |
|---|---|---|---|---|---|
| 1 | 21 | 26.31 | 29.75 | 7.28 | 0.00 |
| 2 | 26 | 18.95 | 19.70 | 4.71 | 0.00 |
| 3 | 35 | 22.16 | 25.47 | 6.10 | 0.00 |
| 6 | 5 | 38.58 | 38.08 | 3.38 | 0.63 |
| 14 | 35 | 18.76 | 18.65 | 2.16 | 0.18 |
| 15 | 21 | 19.55 | 19.96 | 2.35 | 0.37 |
| 16 | 9 | 24.87 | 26.69 | 5.96 | 0.02 |
| 18 | 5 | 22.36 | 22.38 | 1.43 | 0.59 |
| 20 | 4 | 23.11 | 23.12 | 0.46 | 0.07 |
| 22 | 131 | 18.89 | 19.59 | 3.01 | 0.00 |
| 23 | 152 | 18.98 | 19.22 | 3.63 | 0.00 |
| 24 | 2 | 37.66 | 37.66 | 4.43 | |
| 26 | 1 | 24.11 | 24.11 | | |
| 27 | 9 | 20.31 | 20.26 | 0.89 | 0.33 |
| 28 | 25 | 24.63 | 24.76 | 4.34 | 0.09 |
| 30 | 116 | 25.23 | 23.67 | 5.68 | 0.00 |
| 31 | 2096 | 16.13 | 16.44 | 2.01 | 0.00 |
| 32 | 47 | 24.58 | 24.39 | 1.83 | 0.50 |
| 33 | 84 | 21.09 | 21.98 | 3.93 | 0.00 |
| 34 | 113 | 20.20 | 21.01 | 4.18 | 0.00 |
| 36 | 1 | 25.09 | 25.09 | | |
| 37 | 4 | 24.36 | 23.99 | 1.17 | 0.25 |
| 39 | 12 | 22.08 | 21.92 | 1.98 | 0.39 |
| 40 | 3 | 19.46 | 19.59 | 0.47 | 0.55 |
| 42 | 1 | 24.60 | 24.60 | | |
| 43 | 4 | 28.82 | 27.94 | 3.02 | 0.35 |
| 46 | 8 | 21.37 | 21.52 | 1.15 | 0.50 |
| 59 | 764 | 19.07 | 20.02 | 3.74 | 0.00 |
| 65 | 56 | 25.41 | 25.49 | 1.54 | 0.96 |
| 67 | 66 | 18.73 | 18.98 | 1.35 | 0.85 |
| 75 | 273 | 19.18 | 19.23 | 2.28 | 0.00 |
| 76 | 68 | 20.78 | 20.71 | 1.79 | 0.27 |
| 77 | 76 | 19.23 | 19.87 | 4.06 | 0.00 |
| 78 | 34 | 27.78 | 25.38 | 4.82 | 0.00 |
| 79 | 5 | 18.10 | 17.61 | 1.18 | 0.53 |
| 80 | 53 | 20.27 | 21.91 | 6.00 | 0.00 |
| 81 | 46 | 26.48 | 26.44 | 2.20 | 0.00 |

Figure 16

| CROSS DESCRIPTION (#) | SPECIMEN | CATECHIN (mg/g) | EPICATECHIN (mg/g) | TOTAL C+E |
|---|---|---|---|---|
| ALMC5 X MCSG-46 (61) | Whole Seed | 0.36 | 12.62 | 12.97 |
| ALMC5 X MCSG-46 (61) | Whole Seed | 0.23 | 14.37 | 14.60 |
| ALMC5 X MCSG-46 (61) | Whole Seed | 0.27 | 14.41 | 14.68 |
| ALMC5 X MCSG-46 (61) | Whole Seed | 0.34 | 14.99 | 15.33 |
| ALMC5 X MCSG-46 (61) | Whole Seed | 0.28 | 17.39 | 17.67 |
| ALMC5 X MCSG-46 (61) | Whole Seed | 0.15 | 9.58 | 9.73 |
| ALMC5 X MCSG-46 (61) | Whole Seed | 0.24 | 14.86 | 15.10 |
| ALMC5 X MCSG-46 (61) | Whole Seed | 0.00 | 3.12 | 3.12 |
| ALMC5 X MCSG-46 (61) | Whole Seed | 0.38 | 21.98 | 22.36 |
| ALMC5 X MCSG-46 (61) | Whole Seed | 0.26 | 15.85 | 16.12 |
| ALMC5 X MCSG-46 (61) | Whole Seed | 0.05 | 11.72 | 11.77 |
| ALMC5 X MCSG-46 (61) | Whole Seed | 0.20 | 5.58 | 5.78 |
| ALMC5 X MCSG-46 (61) | Whole Seed | 0.18 | 20.52 | 20.70 |
| ALMC5 X MCSG-46 (61) | Whole Seed | 0.34 | 16.60 | 16.94 |
| ALMC5 X MCSG-46 (61) | Whole Seed | 0.05 | 11.61 | 11.66 |
| LCT37A X MCSG-122 (64) | Whole Seed | 0.97 | 38.51 | 39.48 |
| LCT37A X MCSG-122 (64) | Whole Seed | 1.47 | 28.48 | 29.96 |
| LCT37A X MCSG-122 (64) | Whole Seed | 0.54 | 16.31 | 16.85 |
| LCT37A X MCSG-122 (64) | Whole Seed | 1.08 | 19.33 | 20.41 |
| LCT37A X MCSG-122 (64) | Whole Seed | 0.46 | 18.66 | 19.12 |
| LCT37A X MCSG-122 (64) | Whole Seed | 0.37 | 12.86 | 13.24 |
| LCT37A X MCSG-122 (64) | Whole Seed | 0.13 | 17.08 | 17.21 |
| LCT37A X MCSG-122 (64) | Whole Seed | 0.68 | 21.88 | 22.56 |
| LCT37A X MCSG-122 (64) | Whole Seed | 0.94 | 46.34 | 47.28 |
| LCT37A X MCSG-122 (64) | Whole Seed | 0.91 | 47.85 | 48.76 |
| LCT37A X MCSG-122 (64) | Whole Seed | 0.54 | 8.38 | 8.92 |
| LCT37A X MCSG-122 (64) | Whole Seed | 1.46 | 15.87 | 17.33 |
| LCT37A X MCSG-122 (64) | Whole Seed | 0.65 | 18.36 | 19.01 |
| LCT37A X MCSG-122 (64) | Whole Seed | 0.27 | 16.20 | 16.46 |

Figure 17

| CROSS DESCRIPTION (#) | SPECIMEN | MONOMER (mg/g) | DIMER (mg/g) | TRIMER (mg/g) | TETRAMER (mg/g) | PENTAMER (mg/g) | HEXAMER (mg/g) | HEPTAMER (mg/g) | OCTAMER (mg/g) | NONAMER (mg/g) | DECAMER (mg/g) | TOTAL COCOA FLAVANOL (mg/g) |
|---|---|---|---|---|---|---|---|---|---|---|---|---|
| ALMC5 X MCSG-46 (61) | Whole Seed | 13.44 | 9.25 | 11.11 | 13.70 | 15.11 | 15.26 | 10.44 | 10.10 | 8.22 | 6.34 | 112.98 |
| ALMC5 X MCSG-46 (61) | Whole Seed | 15.09 | 10.72 | 13.64 | 17.93 | 20.36 | 21.17 | 15.19 | 15.88 | 13.51 | 10.81 | 154.30 |
| ALMC5 X MCSG-46 (61) | Whole Seed | 15.43 | 11.06 | 14.00 | 18.47 | 21.16 | 21.91 | 15.51 | 15.64 | 12.68 | 9.99 | 155.86 |
| ALMC5 X MCSG-46 (61) | Whole Seed | 16.00 | 10.19 | 12.06 | 14.92 | 16.45 | 16.84 | 11.71 | 11.81 | 9.67 | 7.33 | 126.98 |
| ALMC5 X MCSG-46 (61) | Whole Seed | 18.43 | 12.96 | 15.65 | 19.78 | 21.79 | 22.07 | 15.26 | 15.23 | 12.21 | 9.18 | 162.56 |
| ALMC5 X MCSG-46 (61) | Whole Seed | 10.44 | 7.98 | 9.92 | 13.27 | 15.70 | 16.93 | 12.13 | 12.55 | 10.87 | 8.93 | 118.73 |
| ALMC5 X MCSG-46 (61) | Whole Seed | 15.42 | 11.59 | 14.57 | 18.82 | 21.12 | 21.78 | 15.44 | 15.81 | 13.14 | 10.45 | 158.13 |
| ALMC5 X MCSG-46 (61) | Whole Seed | 3.24 | 2.62 | 3.88 | 5.69 | 7.65 | 9.68 | 7.55 | 8.46 | 8.04 | 6.87 | 63.68 |
| ALMC5 X MCSG-46 (61) | Whole Seed | 22.76 | 15.83 | 18.42 | 22.35 | 23.94 | 23.64 | 16.61 | 17.28 | 14.46 | 11.33 | 186.63 |
| ALMC5 X MCSG-46 (61) | Whole Seed | 16.59 | 11.63 | 13.92 | 17.10 | 18.60 | 18.84 | 12.84 | 12.44 | 10.20 | 8.09 | 140.26 |
| ALMC5 X MCSG-46 (61) | Whole Seed | 12.48 | 10.83 | 13.97 | 18.57 | 21.90 | 23.69 | 17.60 | 19.93 | 17.86 | 15.23 | 172.06 |
| ALMC5 X MCSG-46 (61) | Whole Seed | 6.14 | 4.44 | 4.75 | 6.01 | 6.77 | 7.59 | 5.23 | 4.90 | 4.13 | 3.38 | 53.35 |
| ALMC5 X MCSG-46 (61) | Whole Seed | 20.69 | 16.33 | 19.79 | 26.45 | 29.38 | 29.64 | 21.23 | 21.57 | 17.47 | 14.16 | 216.71 |
| ALMC5 X MCSG-46 (61) | Whole Seed | 17.11 | 13.49 | 15.49 | 20.67 | 23.11 | 23.74 | 16.63 | 16.61 | 13.95 | 11.32 | 172.11 |
| ALMC5 X MCSG-46 (61) | Whole Seed | 12.32 | 9.54 | 11.84 | 15.83 | 18.44 | 20.35 | 14.46 | 14.10 | 11.66 | 9.69 | 138.23 |
| LCT37A X MCSG-122 (64) | Whole Seed | 41.73 | 24.90 | 25.51 | 29.15 | 29.60 | 29.45 | 21.18 | 22.43 | 18.16 | 14.11 | 256.22 |
| LCT37A X MCSG-122 (64) | Whole Seed | 29.60 | 20.27 | 24.41 | 30.35 | 32.14 | 32.00 | 22.91 | 22.67 | 17.48 | 13.36 | 245.21 |
| LCT37A X MCSG-122 (64) | Whole Seed | 17.94 | 12.84 | 16.22 | 21.34 | 24.04 | 24.50 | 17.07 | 16.75 | 13.41 | 10.52 | 174.62 |
| LCT37A X MCSG-122 (64) | Whole Seed | 21.33 | 13.29 | 15.13 | 18.43 | 19.76 | 20.04 | 13.59 | 12.83 | 9.97 | 7.51 | 151.87 |
| LCT37A X MCSG-122 (64) | Whole Seed | 20.46 | 12.92 | 15.46 | 19.43 | 21.25 | 21.38 | 14.47 | 13.38 | 10.24 | 7.83 | 156.82 |
| LCT37A X MCSG-122 (64) | Whole Seed | 14.38 | 8.53 | 10.55 | 13.56 | 15.26 | 15.66 | 10.46 | 9.14 | 6.96 | 5.20 | 109.69 |
| LCT37A X MCSG-122 (64) | Whole Seed | 18.09 | 11.97 | 14.48 | 19.18 | 21.94 | 22.69 | 15.81 | 15.21 | 12.15 | 9.46 | 160.99 |
| LCT37A X MCSG-122 (64) | Whole Seed | 23.06 | 16.18 | 19.42 | 24.63 | 26.75 | 26.63 | 18.25 | 17.72 | 13.56 | 10.26 | 196.48 |
| LCT37A X MCSG-122 (64) | Whole Seed | 50.65 | 30.95 | 31.62 | 35.82 | 36.15 | 35.25 | 26.05 | 28.38 | 23.26 | 18.71 | 316.83 |
| LCT37A X MCSG-122 (64) | Whole Seed | 53.98 | 34.93 | 36.89 | 42.87 | 43.24 | 42.37 | 32.17 | 36.50 | 28.89 | 22.85 | 374.69 |
| LCT37A X MCSG-122 (64) | Whole Seed | 9.80 | 6.61 | 8.09 | 11.17 | 13.79 | 15.54 | 11.00 | 10.94 | 9.44 | 7.51 | 103.90 |
| LCT37A X MCSG-122 (64) | Whole Seed | 18.04 | 11.37 | 12.04 | 14.01 | 14.29 | 13.93 | 8.62 | 7.10 | 5.14 | 3.46 | 108.01 |
| LCT37A X MCSG-122 (64) | Whole Seed | 19.72 | 13.01 | 15.35 | 18.65 | 19.81 | 19.24 | 12.40 | 10.87 | 7.93 | 5.84 | 142.81 |
| LCT37A X MCSG-122 (64) | Whole Seed | 18.00 | 12.82 | 15.03 | 19.37 | 21.45 | 21.80 | 14.65 | 13.58 | 10.50 | 8.19 | 155.39 |

Figure 18A

| CLONE |
|---|
| ALMC5 |
| P7-B |
| ICS39 |
| NA168 |
| ALMC3 |
| IP268 |
| ICS40 |
| NO34 |
| UF 677 |
| NA45 |
| EET400 |
| P10B |
| PH85 |
| COCA 3370/5 |
| GU114 |
| AMAZ 12/4 |
| FADA100 |
| LCT 37F |
| RB37 |
| AMAZ 1515 |
| CA-14 |
| CAB-0022 |
| CAB-0266 |
| CCN 10 |
| CCN 51 |
| COMUM |
| GU-296H |
| HUALLAGA-7 |
| HUALLAGA-9 |
| IAC-1 |
| IP-38 |
| LCTEEN-1621010 |
| LCTEEN-37A |
| LCTEEN-37G |
| MOQ4 25 |
| PAIN9 316 |

Figure 18B

| |
|---|
| PAQUETA 01 |
| PH 123 |
| PH 9 |
| RB 39 |
| ROSA MARIA |
| S.THIAGO |
| SC-1 |
| SJ-02 |
| UF-667 |
| VB-1151 |
| VB-1156 |
| VB-276 |
| VB-515 |
| AMAZ 6.3 |
| SUBCANUM |
| MCSG 17 |
| MCSG 122 |
| MCSG 174 |
| MCSG 134 |
| MCSG 74 |
| MCSG 148 |
| MCSG 36 |
| MCSG 42 |
| MCSG 101 |
| MCSG 30 |
| MCSG 46 |
| MCSG 69 |
| MCSG 89 |
| MCSG 95 |
| MCSG 11 |
| MCSG 139 |
| MCSG 150 |
| MCSG 173 |
| MCSG 2 |
| MCSG 28 |
| MCSG 3 |
| MCSG 37 |
| MCSG 41 |
| MCSG 47 |
| MCSG 98 |
| MCSG 35 |

Figure 19A

| CODE | CROSSES | |
|---|---|---|
| 01 | ALMC-3 | MSCG-69 |
| 02 | ALMC-5 | MCSG-42 |
| 03 | AMAZ-12/4 | MCSG-101 |
| 04 | AMAZ-6.3 | MCSG-41 |
| 06 | CAB-0022 | MCSG-28 |
| 07 | CAB-0266 | MCSG-98 |
| 09 | COMUM | MCSG-2 |
| 10 | CCN-10 | MCSG-3 |
| 11 | CCN-51 | MCSG-41 |
| 12 | COCA-3370/5 | MCSG-37 |
| 14 | EET-400 | MCSG-42 |
| 15 | NA-45 | MCSG-36 |
| 16 | FADA-100 | MCSG-122 |
| 17 | GU-114 | MCSG-42 |
| 18 | GU-296H | MCSG-101 |
| 19 | HUALLAGA-7 | MCSG-101 |
| 20 | HUALLAGA-9 | MCSG-46 |
| 21 | IAC-1 | MCSG-37 |
| 22 | ICS-39 | MCSG-69 |
| 23 | ICS-40 | MCSG-89 |
| 24 | IP-268 | MCSG-41 |
| 25 | IP-38 | MCSG-41 |
| 26 | CTEEN-162101 | MCSG-41 |
| 27 | LCTEEN-37A | MCSG-46 |
| 28 | LCTEEN-37F | MCSG-89 |
| 29 | LCTEEN-37G | MCSG-3 |
| 30 | NA-168 | MCSG-89 |
| 31 | NA-45 | MCSG-122 |
| 32 | NO-34 | MCSG-89 |
| 33 | P-10B | MCSG-122 |
| 34 | P-7B | MCSG-69 |
| 35 | PAQUETA-01 | MCSG-98 |
| 36 | PH-123 | MCSG-41 |
| 37 | PH-85 | MCSG-148 |
| 38 | RB-37 | MCSG-74 |

Figure 19B

| 39 | RB-39 | MCSG-46 |
|---|---|---|
| 40 | ROSA MARIA | MCSG-11 |
| 41 | SC-1 | MCSG-69 |
| 42 | SJ-02 | MCSG-122 |
| 43 | UF-667 | MCSG-95 |
| 44 | UF-677 | MCSG-95 |
| 45 | VB-1151 | MCSG-150 |
| 46 | VB-1156 | MCSG-2 |
| 47 | VB-276 | MCSG-2 |
| 48 | VB-515 | MCSG-46 |
| 49 | CCN-10 | MCSG-41 |
| 50 | ALMC-5 | MCSG-30 |
| 51 | UF-677 | MCSG-134 |
| 52 | NA-168 | MCSG-36 |
| 53 | COCA-3370/5 | MCSG-139 |
| 54 | IP-268 | MCSG-95 |
| 55 | GU-114 | MCSG-174 |
| 56 | ALMC-3 | MCSG-35 |
| 57 | LCTENN-37/G | MCSG-173 |
| 58 | CTEEN-162101 | MCSG-47 |
| 59 | NA-45 | MCSG-46 |
| 60 | EET-400 | MCSG-46 |
| 61 | ALMC-5 | MCSG-46 |
| 62 | NA-168 | MCSG-122 |
| 63 | MOQ-4.25 | MCSG-46 |
| 64 | LCT-37A | MCSG-122 |
| 65 | ALMC-5 | MCSG-122 |
| 66 | AMAZ-1515 | MCSG-122 |
| 67 | P-7B | MCSG-122 |
| 69 | ROSA MARIA | MCSG-46 |
| 70 | AMAZ-1515 | MCSG-46 |
| 71 | NA-45 | SUBCANUM |
| 72 | PAIN - 9.316 | MCSG-46 |
| 74 | ICS 40 | MCSG 46 |
| 75 | EET-400 | MCSG 122 |
| 76 | ICS 40 | MCGS 122 |
| 77 | P 10B | MCGS 46 |
| 78 | CCN-51 | MCGS 46 |
| 79 | PH-9 | MCGS 46 |
| 80 | CA-1.4 | MCGS 46 |
| 81 | S. THIAGO | MCGS 47 |

Figure 20A

| CLONE | w17s189 (T/C) | w7s104 (T/A) | w3s463 (C/G) | w3s41 (G/T) | w3s558 (A/G) | e0050s274 (C/T) | Tir8_339 (C/A) | w11_867 (T/C) | w8s131 (T/C) Sonda 119 | c5s639 (A/G) | CIR222s296 (T/C) | w8s131 (T/C) Sonda 131 | c3s595 (C/A) | c4s123 (G/A) | c4s536 (G/A) | CIR160s384 (G/A) | CIR211s1036 (T/A) | CIR222s296 (Sonda 316) (G/T) | CIR37s112 (G/C) | w8s204/w8s288 (T/C) | w8s288 (G/A) | Est_4785_737 (C/T) |
|---|---|---|---|---|---|---|---|---|---|---|---|---|---|---|---|---|---|---|---|---|---|---|
| ALMC-5 | H | A | C | H | A | C | H | H | T | H | T | C | H | A | G | A | H | T | H | T | G | T |
| P7-B | H | A | H | G | H | C | C | C | C | A | T | C | A | A | A | A | H | T | H | C | G | H |
| ICS39 | H | H | H | H | H | H | C | H | H | A | T | C | C | H | H | A | H | H | G | H | G | T |
| NA168 | H | A | C | G | A | C | C | C | C | A | T | C | A | A | G | A | T | T | H | C | G | H |
| ALMC3 | H | A | C | T | A | C | A | C | H | H | T | H | C | A | G | A | T | T | G | T | H | T |
| IP268 | H | A | H | H | H | C | H | H | H | H | T | H | C | A | G | A | H | H | G | T | H | T |
| ICS40 | H | H | H | H | H | H | C | H | H | A | T | C | C | H | H | A | H | H | G | H | G | T |
| NO34 | H | H | C | T | A | H | A | C | H | H | T | H | C | A | G | A | T | H | G | T | H | H |
| UF 677 | H | H | H | H | H | H | C | H | H | A | T | C | C | H | H | A | H | H | G | H | G | T |
| NA45 | T | A | G | G | H | C | C | C | C | A | T | C | A | A | G | A | A | T | G | C | G | C |
| EET400 | T | A | G | G | G | C | H | C | C | A | T | C | A | A | H | A | H | T | G | H | G | H |
| P10B | T | A | G | G | G | C | C | C | C | A | T | C | A | A | H | A | H | T | G | H | G | H |
| PH85 | T | A | H | H | H | C | H | T | H | A | T | C | C | G | A | A | H | G | G | H | G | T |
| COCA 3370/5 | C | A | G | G | G | H | C | C | C | A | T | C | A | A | G | A | H | T | G | C | G | H |
| GU114 | C | A | G | G | G | C | C | C | C | A | T | C | A | A | G | G | T | G | G | T | G | C |
| AMAZ 12/4 | C | A | C | H | H | C | C | C | C | A | T | C | A | A | G | A | H | H | G | C | G | C |
| FADA 100 | C | A | H | H | H | C | H | C | H | H | T | H | C | A | G | A | T | H | G | T | H | C |
| LCT 37F | C | H | C | H | A | C | C | C | C | A | T | T | C | A | H | A | T | H | G | H | H | H |
| RB37 | C | A | C | T | A | C | C | C | C | A | T | C | A | A | G | A | T | T | G | T | G | C |
| AMAZ 1515 | C | A | C | G | A | C | NA | T | C | A | T | C | A | A | G | A | T | H | G | C | G | C |
| CA-14 | C | H | H | H | H | C | NA | H | C | H | T | H | C | A | G | A | H | H | G | H | H | H |
| CAB-0022 | T | A | G | G | G | C | NA | C | C | A | T | C | A | A | G | A | H | T | G | G | C | G | T |
| CAB-0266 | C | A | H | G | H | C | NA | C | H | A | T | C | A | A | G | A | T | T | G | H | G | C |
| CCN 10 | H | H | H | G | H | C | NA | C | H | H | T | C | C | H | A | A | H | T | G | H | G | H |
| CCN 51 | H | H | G | G | G | C | NA | H | C | A | T | C | A | H | H | A | H | T | G | H | G | H |
| COMUM | T | A | G | G | G | C | NA | T | H | A | T | C | A | A | G | H | H | G | G | H | G | T |
| GU-296H | C | A | G | G | G | C | NA | C | C | A | T | C | A | A | G | G | T | G | G | T | G | C |
| HUALLAGA-7 | C | A | C | T | G | C | NA | C | C | A | T | C | A | A | G | A | T | T | G | H | G | C |
| HUALLAGA-9 | H | A | C | G | A | C | NA | H | C | A | T | C | A | A | G | A | H | T | G | H | G | C |
| IAC-1 | C | H | C | T | A | H | NA | H | H | H | T | H | C | H | H | A | H | H | G | T | H | T |
| IP 38 | H | A | H | H | H | C | NA | H | H | H | T | H | C | A | G | A | H | H | G | T | H | H |
| LCTEEN-1621010 | C | A | G | G | G | H | NA | C | C | A | T | C | A | A | G | A | H | T | G | C | G | H |
| LCTEEN-37 A | C | H | C | G | A | C | NA | C | H | A | T | C | A | H | A | H | A | T | T | G | T | H | H |
| LCTEEN-37G | C | H | C | G | A | C | NA | C | C | A | T | C | A | H | A | T | T | G | T | H | C |
| MOQ 4.25 | C | H | H | H | H | C | NA | H | C | A | H | C | A | A | G | A | H | H | H | H | G | H |
| PAIN 9.316 | T | A | H | H | H | C | NA | H | H | A | T | C | A | A | G | A | H | G | G | G | H |

Figure 20B

| | | | | | | | | | | | | | | | | | | | | | |
|---|---|---|---|---|---|---|---|---|---|---|---|---|---|---|---|---|---|---|---|---|---|
| PAQUETA 01 | H | H | H | H | H | C | NA | C | H | H | T | H | C | A | G | A | T | T | G | T | H | T |
| PH 123 | C | A | H | H | H | H | NA | H | C | H | T | H | C | A | G | A | T | T | G | H | H | H |
| PH 9 | H | A | H | H | H | H | NA | C | H | A | T | H | C | A | G | A | A | G | G | T | H | T |
| RB 39 | C | A | C | H | A | C | NA | C | C | H | T | C | A | G | A | T | T | G | T | G | C |
| ROSA MARIA | H | A | C | T | A | C | NA | C | H | H | T | H | C | A | G | A | H | T | H | T | H | C |
| S.THIAGO | T | A | H | H | H | C | NA | H | H | A | T | C | A | A | G | A | H | G | G | H | G | T |
| SC-1 | H | H | H | H | H | H | NA | H | H | A | T | C | C | H | H | A | H | H | G | H | G | T |
| SJ-02 | C | A | C | H | A | C | NA | C | C | H | T | H | C | A | G | A | T | H | G | T | H | H |
| UF-667 | H | H | H | H | H | H | C | H | H | A | T | C | C | H | H | A | H | H | G | H | G | T |
| VB-1151 | C | A | G | G | G | C | NA | H | H | H | T | C | C | A | G | A | H | G | G | T | G | H |
| VB-1156 | H | A | H | H | H | C | NA | H | H | H | T | H | C | A | G | A | H | H | G | T | H | H |
| VB-276 | H | H | C | T | A | H | NA | H | C | H | T | C | C | H | H | A | H | T | G | C | G | H |
| VB-515 | H | A | C | H | A | C | NA | H | C | A | T | H | A | A | G | A | H | T | G | T | H | H |
| AMAZ 6.3 | C | A | NA | G | A | C | NA | H | C | A | T | C | C | A | G | NA | H | T | G | C | G | C |
| SUBCANUM | C | NA | NA | G | A | NA | NA | T | C | A | T | C | A | NA | NA | A | T | NA | NA | NA | NA | NA |
| MCSG 17 | C | NA | NA | G | A | T | NA | T | C | A | T | C | A | NA | NA | A | T | NA | NA | T | NA | NA |
| MCSG 122 | C | NA | NA | G | A | T | NA | T | C | A | T | C | A | NA | NA | A | T | NA | NA | T | NA | NA |
| MCSG 174 | C | NA | NA | G | A | T | NA | T | C | A | T | C | A | NA | NA | A | T | NA | NA | T | NA | NA |
| MCSG 134 | C | NA | NA | G | A | T | NA | T | C | A | T | C | A | NA | NA | A | T | NA | NA | T | NA | NA |
| MCSG 74 | C | NA | NA | G | A | T | NA | T | C | A | T | C | A | NA | NA | A | T | NA | NA | T | NA | NA |
| MCSG 148 | C | NA | NA | G | A | T | NA | T | C | A | T | C | A | NA | NA | A | T | NA | NA | T | NA | NA |
| MCSG 36 | C | NA | NA | G | A | T | NA | T | C | A | T | C | A | NA | NA | A | T | NA | NA | T | NA | NA |
| MCSG 42 | C | NA | NA | G | A | T | NA | T | C | A | T | C | A | NA | NA | A | T | NA | NA | T | NA | NA |
| MCSG 101 | C | NA | NA | G | A | T | NA | T | C | A | T | C | A | NA | NA | A | T | NA | NA | T | NA | NA |
| MCSG 30 | C | NA | NA | G | A | T | NA | T | C | A | T | C | A | NA | NA | A | T | NA | NA | T | NA | NA |
| MCSG 46 | C | NA | NA | G | A | T | NA | T | C | A | T | C | A | NA | NA | A | T | NA | NA | T | NA | NA |
| MCSG 69 | C | NA | NA | G | A | T | NA | T | C | A | T | C | A | NA | NA | A | T | NA | NA | T | NA | NA |
| MCSG 89 | C | NA | NA | G | A | T | NA | T | C | A | T | C | A | NA | NA | A | T | NA | NA | T | NA | NA |
| MCSG 95 | C | NA | NA | G | A | T | NA | T | C | A | T | C | A | NA | NA | A | T | NA | NA | T | NA | NA |
| MCSG 11 | C | NA | NA | G | A | T | NA | T | C | A | T | C | A | NA | NA | A | T | NA | NA | T | NA | NA |
| MCSG 139 | C | NA | NA | G | A | T | NA | T | C | A | T | C | A | NA | NA | A | T | NA | NA | T | NA | NA |
| MCSG 150 | C | NA | NA | G | A | T | NA | T | C | A | T | C | A | NA | NA | A | T | NA | NA | T | NA | NA |
| MCSG 173 | C | NA | NA | G | A | T | NA | T | C | A | T | C | A | NA | NA | A | T | NA | NA | T | NA | NA |
| MCSG 2 | C | NA | NA | G | A | T | NA | T | C | A | T | C | A | NA | NA | A | T | NA | NA | T | NA | NA |
| MCSG 28 | C | NA | NA | G | A | T | NA | T | C | A | T | C | A | NA | NA | A | T | NA | NA | T | NA | NA |
| MCSG 3 | C | NA | NA | G | A | T | NA | T | C | A | T | C | A | NA | NA | A | T | NA | NA | T | NA | NA |
| MCSG 37 | C | NA | NA | G | A | T | NA | T | C | A | T | C | A | NA | NA | A | T | NA | NA | T | NA | NA |
| MCSG 41 | C | NA | NA | G | A | T | NA | T | C | A | T | C | A | NA | NA | A | T | NA | NA | T | NA | NA |
| MCSG 47 | C | NA | NA | G | A | T | NA | T | C | A | T | C | A | NA | NA | A | T | NA | NA | T | NA | NA |
| MCSG 98 | C | NA | NA | G | A | T | NA | T | C | A | T | C | A | NA | NA | A | T | NA | NA | T | NA | NA |
| MCSG 35 | C | NA | NA | G | A | T | NA | T | C | A | T | C | A | NA | NA | A | T | NA | NA | T | NA | NA |

Figure 21A

| CODE | CROSSES | | w17s189 (T/C) | w3s41 (G/T) | w3s558 (A/G) | e0050s274 (C/T) | w11_867 (T/C) | w8s131 (T/C) Sonda 119 | w8s131 (T/C) Sonda 131 | c3s595 (C/A) | CIR160s384 (G/A) | CIR211s1036 (T/A) | w8s204/w8s288 (T/C) |
|---|---|---|---|---|---|---|---|---|---|---|---|---|---|
| 01 | ALMC-3 | MSCG-69 | H/C | T/G | A/A | C/T | C/T | H/C | H/C | C/A | A/A | T/T | T/T |
| 02 | ALMC-5 | MCSG-42 | H/C | H/G | A/A | C/T | H/T | T/C | C/C | H/A | A/A | H/T | T/T |
| 03 | AMAZ-12/4 | MCSG-101 | C/C | H/G | H/A | C/T | C/C | C/C | C/C | A/A | A/A | H/T | C/T |
| 04 | AMAZ-6.3 | MCSG-41 | C/C | G/G | A/A | C/T | H/T | C/C | C/C | C/A | NA/A | H/T | C/T |
| 06 | CAB-0022 | MCSG-28 | T/C | G/G | G/A | C/T | C/T | C/C | C/C | A/A | H/A | T/T | C/T |
| 07 | CAB-0266 | MCSG-98 | C/C | G/G | H/A | C/T | C/T | H/C | C/C | A/A | A/A | T/T | H/T |
| 09 | COMUM | MCSG-2 | T/C | G/G | G/A | C/T | T/T | H/A | C/C | A/A | H/A | H/T | H/T |
| 10 | CCN-10 | MCSG-3 | H/C | G/G | H/A | C/T | C/T | H/C | C/C | C/A | A/A | H/T | H/T |
| 11 | CCN-51 | MCSG-41 | H/C | G/G | G/A | C/T | H/T | C/C | C/C | A/A | A/A | H/T | H/T |
| 12 | COCA-3370/5 | MCSG-37 | C/C | G/G | G/A | H/T | C/T | C/C | C/C | A/A | A/A | H/T | C/T |
| 14 | EET-400 | MCSG-42 | T/C | G/G | G/A | C/T | C/T | C/C | C/C | C/A | A/A | H/T | H/T |
| 15 | NA-45 | MCSG-36 | T/C | G/G | H/A | C/T | C/T | C/C | C/C | A/A | A/A | A/T | C/T |
| 16 | FADA-100 | MCSG-122 | C/C | H/G | H/A | C/T | C/T | H/C | H/C | C/A | A/A | T/T | T/T |
| 17 | GU-114 | MCSG-42 | C/C | G/G | G/A | C/T | C/T | C/C | C/C | A/A | G/A | T/T | T/T |
| 18 | GU-296H | MCSG-101 | C/C | G/G | G/A | C/T | C/T | C/C | C/C | A/A | G/A | T/T | T/T |
| 19 | HUALLAGA-7 | MCSG-101 | H/C | G/G | A/A | C/T | H/T | C/C | C/C | A/A | A/A | H/T | H/T |
| 20 | HUALLAGA-9 | MCSG-46 | H/C | G/G | A/A | C/T | H/T | C/C | C/C | A/A | A/A | H/T | H/T |
| 21 | IAC-1 | MCSG-37 | C/C | T/G | A/A | H/T | H/T | H/C | H/C | C/A | A/A | H/T | T/T |
| 22 | ICS-39 | MCSG-69 | H/C | H/G | H/A | H/T | H/T | H/C | C/C | A/A | A/A | H/T | H/T |
| 23 | ICS-40 | MCSG-89 | H/C | H/G | H/A | H/T | H/T | H/C | C/C | C/A | A/A | H/T | H/T |
| 24 | IP-268 | MCSG-41 | H/C | H/G | H/A | C/T | H/T | H/C | H/C | C/A | A/A | H/T | T/T |
| 25 | IP-38 | MCSG-41 | H/C | H/G | H/A | C/T | H/T | H/C | H/C | C/A | A/A | H/T | T/T |
| 26 | CTEEN-162101 | MCSG-41 | C/C | G/G | G/A | H/T | C/T | C/C | C/C | A/A | A/A | H/T | C/T |
| 27 | LCTEEN-37A | MCSG-46 | C/C | G/G | A/A | C/T | C/T | C/C | H/C | C/A | A/A | T/T | T/T |
| 28 | LCTEEN-37F | MCSG-89 | C/C | H/G | A/A | C/T | C/T | C/C | T/C | C/A | A/A | T/T | H/T |
| 29 | LCTEEN-37G | MCSG-3 | C/C | G/G | A/A | C/T | C/T | C/C | H/C | C/A | A/A | T/T | T/T |
| 30 | NA-168 | MCSG-89 | H/C | G/G | A/A | C/T | C/T | C/C | C/C | C/A | A/A | T/T | C/T |
| 31 | NA-45 | MCSG-122 | T/C | G/G | H/A | C/T | C/T | C/C | C/C | A/A | A/A | A/T | C/T |
| 32 | NO-34 | MCSG-89 | H/C | T/G | A/A | H/T | C/T | H/C | C/C | C/A | A/A | T/T | T/T |
| 33 | P-10B | MCSG-122 | T/C | G/G | G/A | C/T | C/T | C/C | C/C | C/A | A/A | H/T | H/T |
| 34 | P-7B | MCSG-69 | H/C | G/G | H/A | C/T | C/T | C/C | C/C | A/A | A/A | H/T | C/T |
| 35 | PAQUETA-01 | MCSG-98 | H/C | H/G | H/A | C/T | C/T | H/C | C/C | C/A | A/A | T/T | T/T |
| 36 | PH-123 | MCSG-41 | C/C | H/G | H/A | H/T | H/T | C/C | H/C | C/A | A/A | T/T | H/T |
| 37 | PH-85 | MCSG-148 | T/C | H/G | H/A | C/T | T/T | H/C | C/C | C/A | A/A | H/T | H/T |
| 38 | RB-37 | MCSG-74 | C/C | T/G | A/A | C/T | C/T | C/C | C/C | A/A | A/A | T/T | T/T |

Figure 21B

| 39 | RB-39 | MCSG-46 | C/C | H/G | A/A | C/T | C/T | C/C | C/C | A/A | A/A | T/T | T/T |
|---|---|---|---|---|---|---|---|---|---|---|---|---|---|
| 40 | ROSA MARIA | MCSG-11 | H/C | T/G | A/A | C/T | C/T | H/C | H/C | C/A | A/A | H/T | T/T |
| 41 | SC-1 | MCSG-69 | H/C | H/G | H/A | H/T | H/T | H/C | C/C | C/A | A/A | H/T | H/T |
| 42 | SJ-02 | MCSG-122 | C/C | H/G | A/A | C/T | C/T | C/C | H/C | C/A | A/A | T/T | T/T |
| 43 | UF-667 | MCSG-95 | ***/C | ***/G | ***/A | ***/T | H/T | H/C | ***/C | C/A | A/A | H/T | H/T |
| 44 | UF-677 | MCSG-95 | H/C | H/G | H/A | H/T | H/T | H/C | C/C | C/A | A/A | H/T | H/T |
| 45 | VB-1151 | MCSG-150 | C/C | G/G | G/A | C/T | H/T | H/C | C/C | C/A | A/A | H/T | T/T |
| 46 | VB-1156 | MCSG-2 | H/C | H/G | H/A | C/T | H/T | H/C | H/C | C/A | A/A | H/T | T/T |
| 47 | VB-276 | MCSG-2 | H/C | T/G | A/A | H/T | H/T | C/C | C/C | C/A | A/A | H/T | C/T |
| 48 | VB-515 | MCSG-46 | H/C | H/G | A/A | C/T | H/T | C/C | H/C | A/A | A/A | H/T | T/T |
| 49 | CCN-10 | MCSG-41 | H/C | G/G | H/A | C/T | C/T | H/C | C/C | C/A | A/A | H/T | H/T |
| 50 | ALMC-5 | MCSG-30 | H/C | H/G | A/A | C/T | H/T | T/C | C/C | H/A | A/A | H/T | T/T |
| 51 | UF-677 | MCSG-134 | H/C | H/G | H/A | H/T | H/T | H/C | C/C | C/A | A/A | H/T | H/T |
| 52 | NA-168 | MCSG-36 | H/C | G/G | A/A | C/T | C/T | C/C | C/C | A/A | A/A | T/T | C/T |
| 53 | COCA-3370/5 | MCSG-139 | C/C | G/G | G/A | H/T | C/T | C/C | C/C | A/A | A/A | H/T | C/T |
| 54 | IP-268 | MCSG-95 | H/C | H/G | H/A | C/T | H/T | H/C | C/C | C/A | A/A | H/T | T/T |
| 55 | GU-114 | MCSG-174 | C/C | G/G | G/A | C/T | C/T | C/C | C/C | A/A | G/A | T/T | T/T |
| 56 | ALMC-3 | MCSG-35 | H/C | T/G | A/A | C/T | C/T | H/C | H/C | C/A | A/A | T/T | T/T |
| 57 | LCTENN-37/G | MCSG-173 | C/C | G/G | A/A | C/T | C/T | C/C | H/C | C/A | A/A | T/T | T/T |
| 58 | CTEEN-162101 | MCSG-47 | C/C | G/G | G/A | H/T | C/T | C/C | C/C | A/A | A/A | H/T | C/T |
| 59 | NA-45 | MCSG-46 | T/C | G/G | H/A | C/T | C/T | C/C | C/C | A/A | A/A | A/T | C/T |
| 60 | EET-400 | MCSG-46 | T/C | G/G | G/A | C/T | C/T | C/C | C/C | C/A | A/A | H/T | H/T |
| 61 | ALMC-5 | MCSG-46 | H/C | H/G | A/A | C/T | H/T | T/C | C/C | H/A | A/A | H/T | T/T |
| 62 | NA-168 | MCSG-122 | H/C | G/G | A/A | C/T | C/T | C/C | C/C | A/A | A/A | T/T | C/T |
| 63 | MOQ-4.25 | MCSG-46 | C/C | H/G | H/A | C/T | C/T | C/C | C/C | A/A | A/A | H/T | H/T |
| 64 | LCT-37A | MCSG-122 | C/C | G/G | A/A | C/T | C/T | C/C | C/C | H/C | A/A | T/T | T/T |
| 65 | ALMC-5 | MCSG-122 | H/C | H/G | A/A | C/T | H/T | T/C | C/C | H/A | A/A | H/T | T/T |
| 66 | AMAZ-1515 | MCSG-122 | C/C | G/G | A/A | C/T | T/T | C/C | C/C | A/A | A/A | T/T | C/T |
| 67 | P-7B | MCSG-122 | H/C | G/G | H/A | C/T | C/T | C/C | C/C | A/A | A/A | H/T | C/T |
| 69 | ROSA MARIA | MCSG-46 | H/C | T/G | A/A | C/T | C/T | H/C | H/C | C/A | A/A | H/T | T/T |
| 70 | AMAZ-1515 | MCSG-46 | C/C | G/G | A/A | C/T | T/T | C/C | C/C | A/A | A/A | T/T | C/T |
| 71 | NA-45 | SUBCANUM | T/C | G/G | H/A | C/NA | C/T | C/C | C/C | A/A | A/A | A/T | C/NA |
| 72 | PAIN - 9.316 | MCSG-46 | T/C | H/G | H/A | C/T | C/T | C/C | C/C | A/A | A/A | H/T | H/T |
| 74 | ICS 40 | MCSG 46 | H/C | H/G | H/A | H/T | H/T | H/C | C/C | C/A | A/A | H/T | H/T |
| 75 | EET-400 | MCGS 122 | T/C | G/G | G/A | C/T | C/T | C/C | C/C | C/A | A/A | H/T | H/T |
| 76 | ICS 40 | MCGS 122 | H/C | H/G | H/A | C/T | H/T | H/C | C/C | C/A | A/A | H/T | H/T |
| 77 | P 10B | MCGS 46 | T/C | G/G | A/A | C/T | C/T | C/C | C/C | C/A | A/A | H/T | H/T |
| 78 | CCN-51 | MCGS 46 | H/C | G/G | G/A | C/T | C/T | C/C | C/C | A/A | A/A | H/T | H/T |
| 79 | PH-9 | MCGS 46 | H/C | H/G | H/A | H/T | C/T | H/C | H/C | C/A | A/A | A/T | T/T |
| 80 | CA-1.4 | MCGS 46 | C/C | H/G | H/A | C/T | H/T | H/C | H/C | C/A | A/A | H/T | H/T |
| 81 | S. THIAGO | MCGS 47 | T/C | H/G | H/A | C/T | H/T | H/C | C/C | A/A | A/A | H/T | H/T |

Figure 22

| Cross | Parents Mother | Parents Father | w17s189 (T/C) | e0050s274(C/T) | CIR211s1036 (T/A) | w11_867 (T/C) | w8s204/w8s288 (T/C) | c35s95 (C/A) | w3s41 (G/T) | w8s131 (T/C) Sonda 119 | w3s558 (A/G) |
|---|---|---|---|---|---|---|---|---|---|---|---|
| 15 | NA-45 | MCSG-36 | T/C | C/T | A/T | C/T | C/T | A/A | G/G | C/C | H/A |
| 22 | ICS-39 | MCSG-69 | H/C | H/T | H/T | H/T | H/T | C/A | H/G | H/C | H/A |
| 23 | ICS-40 | MCSG-89 | H/C | H/T | H/T | H/T | H/T | C/A | H/G | H/C | H/A |
| 30 | NA-168 | MCSG-89 | H/C | C/T | T/T | C/T | C/T | A/A | G/G | C/C | A/A |
| 31 | NA-45 | MCSG-122 | T/C | C/T | A/T | C/T | C/T | A/A | G/G | C/C | H/A |
| 32 | NO-34 | MCSG-89 | H/C | H/T | T/T | C/T | T/T | C/A | T/G | H/C | A/A |
| 33 | P-10B | MCSG-122 | T/C | C/T | H/T | T/T | H/T | C/A | G/G | C/C | G/A |
| 34 | P-7B | MCSG-69 | T/C | C/T | H/T | C/T | C/T | A/A | G/G | C/C | H/A |
| 37 | PH-85 | MCSG-148 | T/C | C/T | A/T | T/T | T/T | C/A | H/G | H/C | H/A |
| 59 | NA-45 | MCSG-46 | H/C | C/T | H/T | H/T | C/T | A/A | G/G | C/C | A/A |
| 65 | ALMC-5 | MCSG-122 | H/C | C/T | H/T | C/T | C/T | H/A | H/G | T/C | A/A |
| 67 | P-7B | MCSG-122 | H/C | C/T | H/T | C/T | C/T | A/A | G/G | C/C | H/A |

HYBRID PLANT PRODUCTS FROM *THEOBROMA* SPECIES AND METHODS OF MAKING THE SAME

CROSS-REFERENCE TO RELATED APPLICATIONS

This application is a national stage application, filed under 35 U.S.C. § 371, of International Application No. PCT/US2016/012911, filed Jan. 11, 2016, which claims the benefit of U.S. Provisional Application No. 62/101,917, filed Jan. 9, 2015, both of which are hereby incorporated by reference herein in their entirety for any and all purposes.

REFERENCE TO A SEQUENCE LISTING

The instant application contains a Sequence Listing which has been submitted electronically in ASCII format and is hereby incorporated by reference in its entirety. Said ASCII copy, created on Jan. 11, 2016, is named 029196.00040_SL.txt and is 8,737 bytes in size.

FIELD OF THE INVENTION

Methods for hybridizing members of the *Theobroma* genus in order to form hybrid seeds, plants and plant products are provided. In particular, *Theobroma cacao* and *Theobroma grandiflorum* hybrid seeds, plants and plant products are provided, as well as methods for producing and identifying such hybrid seeds, plants and plant products. Foodstuffs, such as cocoa products obtainable from *Theobroma cacao* and *Theobroma grandiflorum* hybrid seeds, plants and plant products, are also provided, as well as methods for producing such cocoa products.

BACKGROUND OF THE INVENTION

The genus *Theobroma* contains 22 species classified into six sections according to morphological characteristics: *Andropetalum; Glossopetalum; Oreanthes; Rhytidocarpus; Teimatocarpus;* and *Theobroma* (Cuatrecasas, 1964). Representative species from all sections, except for *Andropetalum* (*T. grandiflorum, T. obovatum, T. subincanum, T. speciosum, T. sylvestre, T. microcarpum, T. bicolor, T. cacao*) occur natively in the Brazilian Amazon.

Cocoa butter fatty acids and triacylglycerols profiles significantly differ among the seed fats from different *Theobroma* species (Carpenter et al., 1994; Gilabert-Escriva et al., 2002). Typical fatty acid compositions for various species of *Theobroma* are set forth in FIG. 1 (taken from Table 2 of Gilabert-Escriva et al.).

Natural hybrids between species of *Theobroma* are rare, but there are reports of occurrence, mainly between species of the *Glossopetalum* section (Silva et al., 2004). Some of these natural putative hybrids (five *T. grandiflorum*×*T. subincanum* trees) still exist in the germplasm collection of CEPLAC in Marituba, Pará state (Silva et al., 2004). Natural hybrids between *T. cacao*×*T. grandiflorum* do not exist.

Experimental hybridization between species of the genus *Theobroma* was first attempted in 1937 in Trinidad, but only a few preliminary results were reported (Posnette 1945). A series of hybridization experiments between Brazilian species of *Theobroma* were performed between 1945 and 1951, by George O'Neill Addison and Rosendo Tavares at the "Instituto Agronômico do Norte", in Belém, Pará, Brazil, including a detailed illustration of those hybrids (Addison & Tavares 1951; 1952). The crosses involved all the Brazilian species of the genus *Theobroma* and the related genus *Herrania* (*H. mariae*).

The hybridization between *Theobroma* species from distinct sections, first thought to be extremely difficult, has been proved possible. There are reports of mature trees from hybrids between species of sections *Glossopetalum* and *Andropetalum* [hybrids between *T. angustifolium* and *T. mammosum*; and between *T. simiarum* and *T. mammosum* obtained at CATIE, Costa Rica (Cuatrecasas 1964)]. Successful interspecific crosses involving *T. cacao* have been obtained, according to reports (Silva et al., 2004), as hybrid pods between *T. cacao*×*T. mammosum, T. cacao*×*T. simiarum*, and *T. cacao*×*T. speciosum*; hybrid seedlings from *T. cacao*×*T. microcarpum* and *T. cacao*×*T. angustifolium*; and adult hybrid plants from *T. cacao*×*T. grandiflorum*. There are also reports of hybrid seedlings of *T. grandiflorum* (section *Glossopetalum*) and *T. cacao* (section *Theobroma*) that were identified primarily based on foliage characteristics (Martinson 1966).

Therefore, interspecific hybrids involving *T. cacao* and other *Theobroma* species have reached various degrees of fruit and plant development (Silva et al. 2004). In general, *T. cacao* has been used as the mother plant, and successful putative hybrid seedlings have been obtained at least from crosses involving *T. microcarpum* (section *Telmatocarpus*), *T. angustifolium* and *T. grandiflorum* (section *Glossopetalum*), but plants have shown arrested development after reaching around 10-15 cm. As such, these putative hybrids, including the reported hybrids of *T. cacao* and *T. grandiflorum*, have thus far resulted in plants not capable of maturing independently or producing flowers, fruit, and/or seeds. Moreover, to date, beans obtained from any such *T. cacao* and *T. grandiflorum* hybrids have not undergone chemical analysis, nor have they been used to produce cocoa products, such as cocoa liquor.

SUMMARY OF EMBODIMENTS OF THE INVENTION

*Theobroma* hybrids, such as *T. cacao* and *T. grandiflorum* hybrids, and parts thereof, such as flowers, are provided, as well as seeds obtained from crossing *T. cacao* and *T. grandiflorum*. Hybrid products, such as seeds obtained from crossing *T. cacao* and *T. grandiflorum*, have modified chemical compositions, such as modified fatty acid content and/or modified alkaloid content compared to *T. cacao* and/or *T. grandiflorum*. In several embodiments, the hybrid products exhibit characteristics, such as decreased palmitic acid as compared to *T. cacao*; and/or decreased theobromine compared to *T. cacao*. In other embodiments, the hybrid products comprise tetramethyluric acid (TMUA). In other embodiments, the hybrids and/or hybrid products comprise and/or one or more for the following Single Nucleotide Polymorphism (SNP) markers: w17s189(T/C), e0050s274(C/T), CIR211s1036(T/A), w11s867(T/C), w8s204(T/C), c3s595 (C/A), w3s41(G/T), w8s131(T/C), w3s558(A/G), and any combination thereof. In yet other embodiments, the hybrid plants and plant products comprise one or more of the above-mentioned characteristics and/or SNP markers.

Methods of producing *Theobroma* hybrids, such as *T. cacao* and *T. grandiflorum* hybrids, and parts thereof, such flowers, are provided, as well as methods of producing seed from crossing *T. cacao* and *T. grandiflorum*. In several embodiments, the methods of producing a *T. cacao* and *T. grandiflorum* hybrid and/or seed of a *T. cacao* and *T. grandiflorum* hybrid comprise crossing a variety of *T. cacao* and *T. grandiflorum* and obtaining seeds therefrom, and selecting seeds and/or plants resulting from the cross. The seeds and/or plants may be selected on the basis of certain characteristics, such as the seeds and/or plants possess decreased palmitic acid as compared to *T. cacao*; decreased theobromine compared to *T. cacao*; the presence of tetramethyluric acid; and/or one or more of the following SNP markers: w17s189(T/C), e0050s274(C/T), CIR211s1036(T/A), w11s867(T/C), w8s204(T/C), c3s595(C/A), w3s41(G/T), w8s131(T/C), w3s558(A/G), and any combination thereof. Hybrid plants and plant products (e.g., seed) produced by these processes are also provided.

In other embodiments, methods for producing a hybrid plant of *Theobroma cacao* and *Theobroma grandiflorum*, comprising (a) determining whether seed produced by crossing a variety of *Theobroma cacao* and a variety of *Theobroma grandiflorum* comprises one or more of the following characteristics: decreased palmitic acid as compared to *T. cacao*; decreased theobromine compared to *T. cacao*; the presence of tetramethyluric acid; and/or one or more of the following SNP markers: w17s189(T/C), e0050s274(C/T), CIR211s1036(T/A), w11s867(T/C), w8s204(T/C), c3s595(C/A), w3s41(G/T), w8s131(T/C), w3s558(A/G), and any combination thereof; and (b) growing seeds comprising one or more of the characteristics and/or SNP markers recited in (a) to obtain a hybrid plant of *Theobroma cacao* and *Theobroma grandiflorum*, are provided. Hybrid plants produced by these processes are also provided.

In other embodiments, methods for producing a hybrid plant of *Theobroma cacao* and *Theobroma grandiflorum*, comprising (a) crossing a variety of *Theobroma cacao* and a variety of *Theobroma grandiflorum* and obtaining seed therefrom; (b) determining whether seed from step (a) comprises one or more of the following characteristics: decreased palmitic acid as compared to *T. cacao*; decreased theobromine compared to *T. cacao*; the presence of tetramethyluric acid; and/or one or more of the following SNP markers: w17s189(T/C), e0050s274(C/T), CIR211s1036(T/A), w11s867(T/C), w8s204(T/C), c3s595(C/A), w3s41(G/T), w8s131(T/C), w3s558(A/G), and any combination thereof; and (c) growing seeds comprising one or more of the characteristics and/or SNP markers recited in (b) to obtain a hybrid plant of *Theobroma cacao* and *Theobroma grandiflorum*, are provided. Hybrid plants produced by these processes are also provided.

In other embodiments, methods for producing a hybrid plant of *T. cacao* and *T. grandiflorum* are provided, which comprises (a) crossing a variety of *Theobroma cacao* and a variety of *Theobroma grandiflorum* and obtaining hybrid seed therefrom; (b) sowing hybrid seeds obtained in a growth medium and incubating them in a growth room until plantlets have been formed; (c) transferring plantlets to a suitable substrate; and (d) optionally grafting hybrid plantlets obtained onto a plant. In other embodiments, after step (a), and before step (b), a sample of the seed is removed and the chemical composition and/or genetic makeup is analyzed. In other embodiments, only seeds that possess certain characteristics, such as the above-mentioned characteristics and/or SNP markers, progress on to step (b). Hybrid plants produced by these processes are also provided.

Methods for identifying, selecting, screening and/or confirming *T. cacao* and/or *T. grandiflorum* hybrid plants or parts thereof, as well as, seeds obtained from *T. cacao* and/or *T. grandiflorum*, are provided. The hybrid plants, plant parts and/or seeds may be identified, selected, screened and/or confirmed on the basis of certain characteristics, such as decreased palmitic acid as compared to *T. cacao*; decreased theobromine compared to *T. cacao*; the presence of tetramethyluric acid; and/or one or more of the following SNP markers: w17s189(T/C), e0050s274(C/T), CIR211s1036(T/A), w11s867(T/C), w8s204(T/C), c3s595(C/A), w3s41(G/T), w8s131(T/C), w3s558(A/G), and any combination thereof. In particular embodiments, the hybrid plants, plant parts and/or seeds may be identified, selected, screened and/or confirmed on the basis of the presence of tetramethyluric acid and/or one or more of the following SNP markers: w17s189(T/C), e0050s274(C/T), CIR211s1036(T/A), w11s867(T/C), w8s204(T/C), c3s595(C/A), w3s41(G/T), w8s131(T/C), w3s558(A/G), and any combination thereof.

Methods of producing a plant comprising (a) selecting a progeny plant resulting from crossing a variety of *Theobroma cacao* and a variety of *Theobroma grandiflorum*, where the progeny plant or seed of the progeny plant exhibits one or more of the following characteristics: decreased palmitic acid as compared to *T. cacao*; decreased theobromine compared to *T. cacao*; the presence of tetramethyluric acid; and/or one or more of the following SNP markers: w17s189(T/C), e0050s274(C/T), CIR211s1036(T/A), w11s867(T/C), w8s204(T/C), c3s595(C/A), w3s41(G/T), w8s131(T/C), w3s558(A/G), and any combination thereof; and (b) crossing the progeny plant with another plant, are provided. In other embodiments, the methods further include a step of crossing a variety of *Theobroma cacao* and a variety of *Theobroma grandiflorum*. In any of the embodiments, the other plant may be *Theobroma cacao* or *Theobroma grandiflorum*, such as one of the parental plants used in crossing *Theobroma cacao* and *Theobroma grandiflorum*.

Methods for analyzing a *Theobroma cacao* and *Theobroma grandiflorum* hybrid or seed obtained by crossing *Theobroma cacao* and *Theobroma grandiflorum*, comprising (a) crossing a variety of *Theobroma cacao* and a variety of *Theobroma grandiflorum* and obtaining seed therefrom; (b) removing a sample of said seed, and (c) analyzing the chemical and/or genetic composition of said seed, are provided. In some embodiments, ⅓ of the seed is removed. In other embodiments, at least 100 mg of the seed is removed. In yet other embodiments, the methods comprise analyzing fatty acids, flavanols, and/or methyl xanthenes. In other embodiments, the methods comprise analyzing palmitic acid, theobromine, and/or tetramethyluric acid. In yet other embodiments, the methods comprise analyzing a SNP marker indicative of a *Theobroma cacao* and *Theobroma grandiflorum* hybrid, such as w17s189 (T/C), e0050s274(C/T), CIR211s1036(T/A), w11s867(T/C), w8s204(T/C), c3s595(C/A), w3s41(G/T), w8s131(T/C), w3s558(A/G), or any combination thereof.

Products obtained by, or derived from, the hybrid plants or hybrid products (e.g., seeds obtained from crossing *T. cacao* and *T. grandiflorum*) described herein, particularly foodstuffs, are provided. In several embodiments, cocoa products, such as cocoa liquor, obtained by processing the fruit obtained from crossing *T. cacao* and *T. grandiflorum* are provided. In other embodiments, cocoa products comprising increased melting and/or crystallization temperatures compared to corresponding cocoa products of *T. cacao* alone are also provided. In yet other embodiments, methods for making cocoa products from the plant products (e.g., seeds obtained from *T. cacao* and *T. grandiflorum*) described herein are provided. In other embodiments, methods for making cocoa products comprising increased melting and/or crystallization temperatures compared to cocoa products from *T. cacao* alone are also provided.

Other features and advantages will become apparent to those skilled in the art upon examination of the following or upon learning by practice of the invention.

BRIEF DESCRIPTION OF THE DRAWINGS

FIG. 1 is a table including the fatty acid profiles of various species of *Theobroma*.

FIG. 2 is a set of photographs illustrating the pollination steps carried out according to one aspect described here, and in which FIG. 2(A) shows the protection applied to the unopened *T. cacao* bud one day before pollination. FIG. 2(B) shows the *Theobroma grandiflorum* flower used as a pollen source, FIG. 2(C) shows the manual pollination procedure, and FIG. 2(D) shows a *T. cacao* flower 5 days after pollination.

FIG. 3 is a series of photographs illustrating a seed collection procedure in accordance with an embodiment described herein, wherein FIG. 3(A) shows pods obtained following pollination as shown in FIG. 2, FIG. 3(B) shows hybrid plants growing in Woody Plant Media, and FIG. 3(C) shows samples of seeds ready to be lyophilized.

FIG. 4 is a series of photographs illustrating the differences between (A) seeds of *T. cacao*, (B) seeds of *T. grandiflorum*, and (C-D) hybrid seeds obtained from the hybrid pods, all without testa.

FIG. 5 is a diagram illustrating the collection of a seed sample for analysis, in which a portion of the cotyledon is used for chemical analysis, and the remaining portion is planted in growth media.

FIGS. 8A-8B are photographs of TcxTg hybrids grafted on top of *T. grandiflorum* rootstocks. FIG. 8A is a photograph of hybrid MCGH-031-011-36, and FIG. 8B is a photograph of hybrid MCGH-023-009-11.

FIG. 9 is a table describing the distribution of palmitic acid content for different hybrid plants assessed using the Shapiro-Wilk test at 5% probability. "Length" indicates the number of seeds that were tested for each specific cross.

FIG. 16 is a table showing the concentrations of catechins and epicatechins present in seeds from two crosses, 61 (corresponding to ALMC5×MCSG-46) and 64 (corresponding to LCT37A×MCSG-122).

FIG. 17 is a table showing the concentrations of total cocoa flavanols present in seeds from two crosses, 61 and 64.

FIGS. 18A and 18B are tables identifying the varieties of *T. cacao* and *T. grandiflorum* used to prepare hybrid plants.

FIGS. 19A and 19B are tables identifying 81 crosses evaluated.

FIGS. 20A and 20B are tables showing the genotypes of *T. cacao* and *T. grandiflorum* used to prepare hybrid plants of 22 Single Nucleotide Polymorphism (SNP) markers.

FIGS. 21A and 21B are tables showing the genotypes of 81 crosses evaluated using 11 SNP markers.

FIG. 22 is a table identifying the possible alleles of 9 SNPs present in the hybrids for 12 different crosses

DETAILED DESCRIPTION OF THE INVENTION

Figure 2:
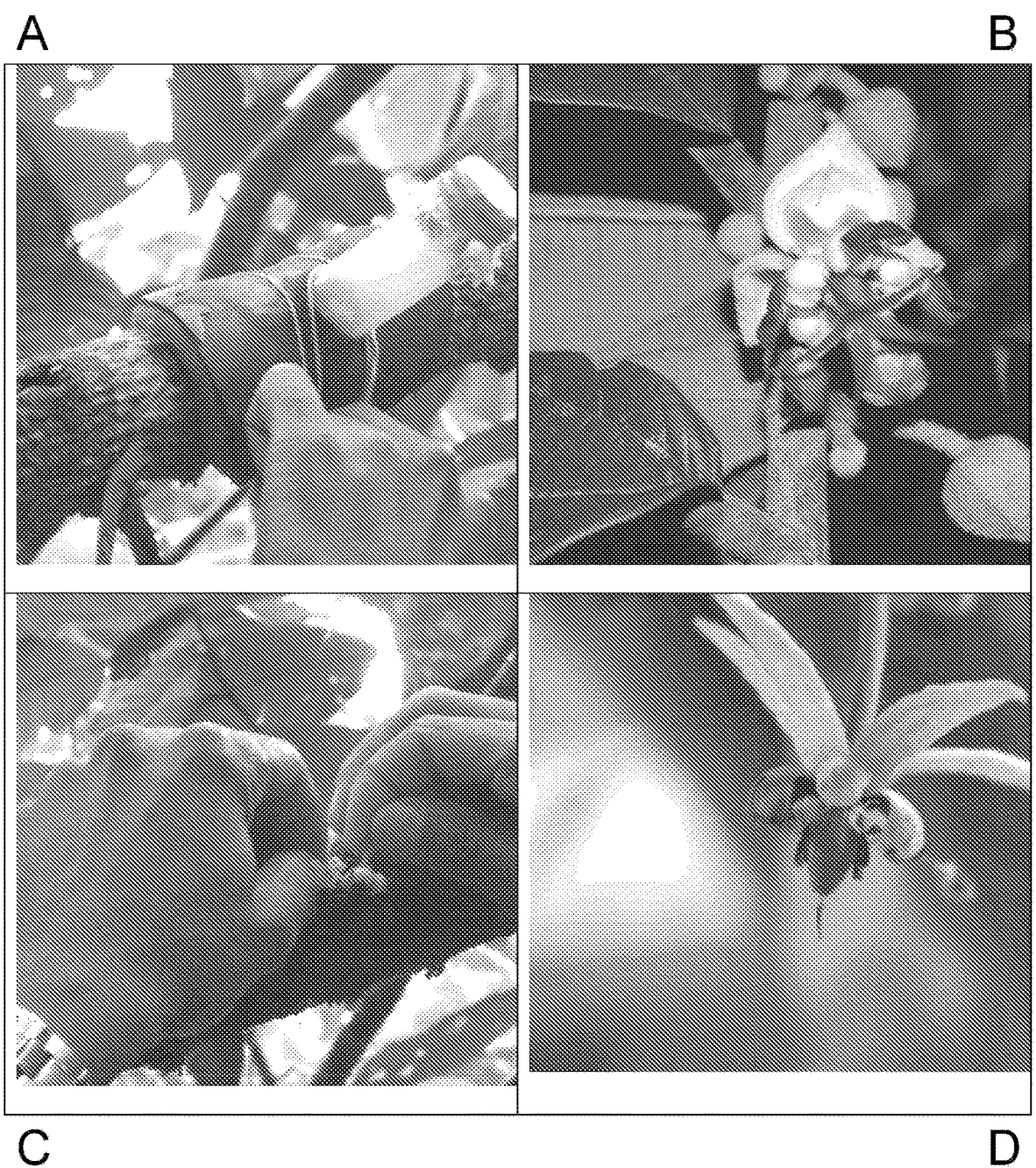

Methods for hybridizing members of the *Theobroma* genus in order to obtain hybrid seeds, plants and plant parts thereof, and particularly to methods for hybridizing *Theobroma cacao* and *Theobroma grandiflorum* are provided. Hybrid seeds and plants, as well as, flower, fruit and seed-bearing hybrids of *Theobroma* are provided. Methods for confirming that the resulting progeny are hybrids, and methods for identifying and/or selecting *Theobroma cacao* and *Theobroma grandiflorum* hybrids are described. Hybrid *Theobroma* plant products, such as seeds obtained from crossing *Theobroma cacao* and *Theobroma grandiflorum*, having modified chemical compositions, such as modified fatty acid content and/or modified alkaloid content are also described. Products derived from the hybrid seeds or plants, particularly foodstuffs, such as cocoa products, are also provided.

The inventors have surprisingly found that *Theobroma cacao* and *Theobroma grandiflorum* hybrid products, such as seeds obtained from crossing *Theobroma cacao* and *Theobroma grandiflorum*, comprise advantageous properties. For example, the inventors obtained *Theobroma cacao* and *Theobroma grandiflorum* hybrid products having decreased palmitic acid compared to *Theobroma cacao*, and/or decreased theobromine compared to *Theobroma cacao*. Moreover, the inventors unexpectedly found *Theobroma cacao* and *Theobroma grandiflorum* hybrid products are suitable for making cocoa products and, for example, have higher melting and crystallization temperatures than *Theobroma cacao*. The inventors have also determined that certain chemical and/or genetic markers can be used to identify and/or select for *Theobroma cacao* and *Theobroma grandiflorum* hybrids.

As used herein, the term "hybrid" encompasses fully hybridized offspring that are heterozygous with respect to the parents, as well as partially hybridized offspring that may result, for example, from genetic translocations.

As used herein, the term "seed" is used interchangeably with the term "bean".

As used herein, the term "pod" is used interchangeably with the term "fruit".

As used herein, the term "heat-resistant cocoa product" means a cocoa product that has a higher melting temperature than a cocoa product made from *Theobroma cacao* alone.

*Theobroma* hybrid products, such as seeds obtained by crossing *Theobroma cacao* and *Theobroma grandiflorum*, and plants grown from such hybrid seeds are provided. Hybrid products are obtained from crossing two different species of *Theobroma*.

The species of *Theobroma* that may be used include *Theobroma angustifolium*, *Theobroma bicolor*, *Theobroma cacao*, *Theobroma canumanense*, *Theobroma grandiflorum*, *Theobroma mammosum*, *Theobroma microcarpum*, *Theobroma obovatum*, *Theobroma simiarum*, *Theobroma speciosum*, *Theobroma stipulatum*, *Theobroma subincanum*, and *Theobroma sylvestre*. Preferred species for use include *Theobroma cacao* and *Theobroma grandiflorum*.

Particular varieties of *Theobroma cacao* that may be used include ALMC 5, P7-B, ICS39, NA168, ALMC 3, IP268, ICS40, NO34, UF 677, NA-45, EET400, P10B, PH85, COCA 3370/5, GU114, AMAZ 12/4, FADA100, LCT 37F, RB37, AMAZ 1515, CA-1.4, CAB-0022, CAB-0266, CCN 10, CCN 51, COMUM, GU-296H, HUALLAGA-7, HUALLAGA-9, IAC-1, IP 38, LCTEEN-1621010, LCTEEN-37A, LCTEEN-37G, MOQ 4.25, PAIN 9 316, PAQUETA 01, PH 123, PH 9, RB 39, ROSA MARIA, S THIAGO, SC-1, SJ-02, UF-667, VB-1151, VB-1156, VB-276, VB-515, and AMAZ 6.3. Of these, preferred varieties include NA-45, ICS-39, ICS-40, NA-168, NO-34, P-10B, P-7B, PH-85, and ALMC-5. Each of the above varieties of *Theobroma cacao* are known in the art, and material (e.g., germplasm) for these varieties can be accessed through various depositories, such as the International Cocoa Germplasm Database (http://www.icgd.rdg.ac.uk/index.php), the International Cocoa Collection (IC3) (http://catie.ac.cden/products-and-services/collections-and-germplasm-banks/international-cocoa-collection), or through the International Cocoa Genebank, Trinidad (ICG,T) (http://sta.uwi.edu/cru/GeneticResources.asp)

Particular varieties of *Theobroma grandiflorum* that may be used in the invention are SUBCANUM, MCSG-17, MCSG-122, MCSG-174, MCSG-134, MCSG-74, MCSG-148, MCSG-36, MCSG-42, MCSG-101, MCSG-30, MCSG-46, MCSG-69, MCSG-89, MCSG-95, MCSG-11, MCSG-139, MCSG-150, MCSG-173, MCSG-2, MCSG-28, MCSG-3, MCSG-37, MCSG-41, MCSG-47, MCSG-98, and MCSG-35. Of these, preferred varieties include MCSG-36, MCSG-69, MCSG-89, MCSG-122, MCSG-148, and MCSG-46. All varieties of *Theobroma grandiflorum* designated as "MCSG" are available through the Mars Center for Cocoa Science, Itajuipe, Brazil. Additional cultivars of *Theobroma grandiflorum* that may be used in the invention are the Mamorano and Mamau cultivars.

Combinations of varieties that may yield hybrid plants according to the invention include the 81 crosses described in FIGS. 19A-19B. Preferred combinations include the 37 crosses described in FIG. 9. Of these, more preferred combinations include NA-45×MCSG-36, ICS-39×MCSG-69, ICS-40×MCSG-89, NA-168×MCSG-89, NA-45×MCSG-122, NO-34×MCSG-89, P-10B×MCSG-122, P-7B×MCSG-69, PH-85×MCSG-148, NA-45×MCSG-46, ALMC-5×MCSG-122, and P-7B×MCSG-122.

In other embodiments, the following hybrid seeds and plants grown from such seeds are provided: MCGH-015-001-13, MCGH-022-002-01, MCGH-022-003-03, MCGH-022-006-04, MCGH-022-020-11, MCGH-023-008-14, MCGH-023-009-01, MCGH-023-009-11, MCGH-023-009-14, MCGH-023-013-02, MCGH-023-014-03, MCGH-023-014-06, MCGH-023-024-14, MCGH-023-037-05, MCGH-023-037-07, MCGH-030-012-04, MCGH-031-006-19, MCGH-031-006-22, MCGH-031-020-16, MCGH-031-028-34, MCGH-031-051-11, MCGH-031-052-34, MCGH-031-057-07, MCGH-031-061-05, MCGH-031-066-01, MCGH-031-066-05, MCGH-031-066-24, MCGH-031-070-10, MCGH-031-072-07, MCGH-031-073-04, MCGH-031-074-14, MCGH-031-079-06, MCGH-031-079-16, MCGH-031-081-02, MCGH-031-092-09, MCGH-031-095-08, MCGH-031-096-04, MCGH-031-103-09, MCGH-031-104-32, MCGH-031-110-15, MCGH-031-111-16, MCGH-031-113-11, MCGH-031-113-19, MCGH-031-116-03, MCGH-031-119-04, MCGH-031-123-18, MCGH-031-124-02, MCGH-031-69-06, MCGH-033-014-01, MCGH-034-002-12, MCGH-034-006-01, MCGH-059-029-03, MCGH-059-041-13, MCGH-065-010-09, MCGH-067-001-41, MCGH-067-002-31, or MCGH-067-003-06. The first three digit number refers to the cross (shown in the first column of FIGS. 19A and 19B), the second three digit number refers to the pod number in that cross, and the two digit number refers to the bean in the specified pod. For example, "MCGH-015-001-13" refers to cross 15 (i.e., NA-45×MCSG-36), "001" refers to pod 1 from cross 15; and "13" refers to seed 13 of pod 1 from cross 15.

In certain aspects, the mother plant used in crossing is *Theobroma cacao*. For example, as shown in FIGS. 2A-2D, pollen of *Theobroma grandiflorum* is applied to the gynoecium (female parts of the flower) of *Theobroma cacao*. The techniques employed for the pollen transfer are known in the art, and typically involve protecting the unopened flowers, for example, with a barrier such as a plastic or glass enclosure (see, e.g., FIG. 2A), for a period of time before and optionally also after, manual pollination. The unopened flowers may be protected, for example, for about one week prior to pollination, preferably 3 days prior to pollination, more preferably about 1 day prior to pollination. The pollinated flower may also optionally be protected, for example, for about 1-3 days after pollination.

The flowers of the pollinated mother plant (see, e.g., FIG. 2D) are then allowed to mature for a period of time suitable to form pods. Pods are harvested and subjected to further processing when they are mature, which typically will be between 100-200 days after pollination, for example between 140 and 160 days after pollination. Examples of pods obtained are shown in FIGS. 3A-3C.

Seeds are recovered from the pods. The seeds are cleaned, and the testa removed, for example, under sterile conditions. A comparison in the appearance of the seeds from *T. cacao*

(FIG. 4A), *T. grandiflorum* (FIG. 4B), and various crosses (FIGS. 4C-4D) is provided by way of example. The appearance of the seeds may optionally be observed as part of the process of determining whether the cross resulted in hybridization.

Seeds may be chemically and/or genetically analyzed. In one aspect, a sample of cotyledon is removed from seeds and the chemical composition and/or genetic makeup of each seed is analyzed, as illustrated in FIG. 5. When chemical and/or genetic analysis is performed, a sufficient amount of material may be removed from the cotyledon to permit the analysis to be conducted without compromising the viability of the remaining seed. In some aspects, about ⅓ of the cotyledon or less is removed for the analysis. In other aspects, 100 mg of lyophilized tissue or more of the seed is used for chemical and/or genetic analysis. The remaining portion of the cotyledon may be grown in a suitable medium, for example, woody plant medium. According to some aspects, only those seeds determined to be hybrids (e.g., using chemical and/or SNP markers) and/or have desired properties (e.g., lower palmitic acid compared to *T. cacao*) are grown to produce plantlets and/or mature plants. According to other aspects, seeds determined to be hybrids (e.g., using chemical and/or SNP markers) and/or that have desired properties (e.g., lower palmitic acid compared to *T. cacao*) are used to make cocoa products. According to other aspects, seeds that are the product of an incomplete hybridization (e.g., translocation events) are grown to produce plantlets and/or mature plants.

Analysis of the chemical composition of the seeds may be carried out to determine the amounts of various fatty acids, flavanols, and/or alkaloids contained therein. Conveniently, the sample may be freeze-dried prior to conducting the chemical analysis, as this facilitates handling and gives accurate analytical results. The amounts of the various chemical components of the seeds may be determined using techniques known to those skilled in the art.

For example, fatty acid content may be analyzed by solvent-based lipid extraction and subsequent quantification using chromatographic techniques (gas chromatography (e.g., GC-FID, GS-MS), gas-liquid chromatography (e.g., GLC-FID, GLC-MS), and high-performance liquid chromatography (HPLC)). See, e.g., Christie, W. W., (1989) Gas Chromatography and Lipids: A Practical Guide, The Oily Press, Dundee; Christie, W. W. (1982) J. Lipid Res., 23, 1072-1075; Ciucanu, I. and Kerek, F., (1984) J. Chromatography, 279, 493-506, each of which is hereby incorporated by reference.

Alkaloid and flavanol content may be analyzed by liquid extraction and subsequent quantification using spectrophotometry (e.g., UV/Visible, IR, NIR, and Raman), chromatography (e.g., HPLC, GS-MS), or capillary electrophoresis. See, e.g., Blauch, J. L. and Stanley, M. T., "Determination of Caffeine and Theobromine in Coffee, Tea and Instant Hot Cocoa Mixes," Journal of Food Science, 48, (1983), pp. 745-747; G. E. Adamson et al., "HPLC method for the Quantification of Procyanidins in Cocoa and Chocolate Samples and Correlation to Total Anti-oxidant Capacity," J. Agric. Food Chem. 47, 1999, 4184-4188; M. A. Kelm et al., "HPLC separation and purification of cacao (*Theobroma cacao* L.) procyanidins according to degree of polymerization using a diol stationary phase," J Agric. Food Chem. 54, 2006, 1571, each of which is hereby incorporated by reference.

Once the chemical composition of the seeds has been analyzed, for example, as shown in FIGS. 9-17, the amounts of various compounds of interest can be compared with the chemical compositions of the parent plants in order to determine, for example, if the seeds are hybrids exhibiting the traits of either or both parental plants. Further, the chemical composition analysis may be used to select seeds that have a chemical composition of interest. For example, the fatty acid profile of the seeds may be compared with the fatty acid profile of one or both of the parents (see FIG. 1), or with another desired chemical composition profile.

For example, according to some aspects, a hybrid of *T. cacao* and *T. grandiflorum* is developed that exhibits a modified fatty acid profile as compared to *T. cacao*. Particular fatty acid modifications include, but are limited to, increased polyunsaturated fatty acid levels (e.g., linoleic acid), and decreased saturated fatty acid levels (e.g., palmitic acid). Also included are increased levels of the saturated fatty acid stearic acid, which is associated with lower LDL-levels than other saturated fatty acids.

According to some aspects, the level of linoleic acid is increased by about 25%-500%, 50%-250%, or 75%-100% compared to *T. cacao* and/or *T. grandiflorum*.

According to other aspects, the level of palmitic acid of any of the hybrids described herein is decreased by about 10%-95%, 25%-75%, or 50%-67% compared to *T. cacao*. In other aspects, the level of palmitic acid is measured as the percentage of the total amount of fatty acids in a sample and is in the range of 7% to 20%, 7% to 19%, 7% to 18%, 7% to 17%, 7% to 16%, or 7% to 15%. In other aspects, the level of palmitic acid is measured as the percentage of the total amount of fatty acids in a sample and is in the range of 10% to 20%, 10% to 19%, 10% to 18%, 10% to 17%, 10% to 16%, or 10% to 15%. In other aspects, the level of palmitic acid is measured as the percentage of the total amount of fatty acids in a sample and is in the range of 5% to 15%, 5% to 12%, or 5% to 10%. In other aspects, the level of palmitic acid is measured as the percentage of the total amount of fatty acids in a sample and is less than 30%, 29%, 28%, 27%, 26%, 25%, 24%, 23%, 22%, 21%, 20%, 19%, 18%, 17%, 16%, 15%, 14%, 13%, 12%, 11%, 10%, 9%, or 8%.

According to still other aspects, the level of stearic acid is increased by about 10%-100%, preferably 20%-70%, more preferably 30%-40% compared to *T. cacao*.

According to further aspects, hybrid seed of *T. cacao* and *T. grandiflorum* is developed that exhibits a modified alkaloid profile as compared to *T. cacao*. Particular alkaloid modifications within the scope of the invention include methyl xanthines (e.g., theobromine, caffeine, and tetramethyluric acid (TMUA, also known as theacrine or ATMU)). According to some aspects, the level of caffeine may be either increased or decreased by about 10%-100%, about 25%-75%, or about 40%-60% compared to *T. cacao*. In some aspects, the level of caffeine in any of the hybrids described herein is between 1-10 mg/g, 2-8 mg/g, or 4-6 mg/g. In *T. cacao*, the level of caffeine is typically between 2-5 mg/g in *Theobroma cacao*.

According to other aspects, the level of theobromine in any of the hybrids described herein is decreased by 10%-100%, 25%-75%, or 40%-60% compared to *T. cacao*. In other aspects, the level of theobromine is less than 5 mg/g, less than 4.5 mg/g, less than 4 mg/g, less than 3.5 mg/g, less than 3 mg/g, less than 2.5 mg/g, less than 2 mg/g, less than 1.5 mg/g, less than 1 mg/g, less than 0.5 mg/g, less than 0.25 mg/g, or less than 0.1 mg/g. In other aspects, the level of theobromine is in the range of 0 mg/g to 5 mg/g, 0.05 mg/g to 5 mg/g, 0.10 mg/g to 5 mg/g, 0.5 mg/g to 5 mg/g, 1 mg/g to 5 mg/g, 1.5 mg/g to 5 mg/g, 2 mg/g to 5 mg/g, 2.5 mg/g to 5 mg/g, 3 mg/g to 5 mg/g. In other aspects, the level of theobromine is in the range of 0 mg/g to 4.5 mg/g, 0.05 mg/g to 4.5 mg/g, 0.10 mg/g to 4.5 mg/g, 0.5 mg/g to 4.5 mg/g, 1 mg/g to 4.5 mg/g, 1.5 mg/g to 4.5 mg/g, 2 mg/g to 4.5 mg/g, 2.5 mg/g to 4.5 mg/g, 3 mg/g to 4.5 mg/g. In other aspects, the level of theobromine is in the range of 0 mg/g to 4 mg/g, 0.05 mg/g to 4 mg/g, 0.10 mg/g to 4 mg/g, 0.5 mg/g to 4 mg/g, 1 mg/g to 4 mg/g, 1.5 mg/g to 4 mg/g, 2 mg/g to 4 mg/g, 2.5 mg/g to 4 mg/g, 3 mg/g to 4 mg/g. In other aspects, the level of theobromine is in the range of 0 mg/g to 3.5 mg/g, 0.05 mg/g to 3.5 mg/g, 0.10 mg/g to 3.5 mg/g, 0.5 mg/g to 3.5 mg/g, 1 mg/g to 3.5 mg/g, 1.5 mg/g to 3.5 mg/g, 2 mg/g to 3.5 mg/g, 2.5 mg/g to 3.5 mg/g, 3 mg/g to 3.5 mg/g. In *T. cacao*, the level of Theobromine is in the range of 15-40 mg/g.

According to still other aspects, the presence TMUA is determined in any of the hybrids or seeds described herein. In some aspects, the level of TMUA is in the range of 0.5 mg/g to 3 mg/g, 0.5 mg/g to 2.5 mg/g, 0.5 mg/g to 2 mg/g, or 0.5 mg/g to 1.5 mg/g. In other aspects, the level of TMUA is 1.0 mg/g to 3 mg/g, 1.0 mg/g to 2.5 mg/g, 1.0 mg/g to 2.0 mg/g, or 1.0 mg/g to 1.5 mg/g. In *T. cacao*, TMUA is not present.

According to still further aspects, hybrid seed of *T. cacao* and *T. grandiflorum* is developed that exhibits a modified flavanol content as compared to *T. cacao*. Particular flavanol content modifications include total flavanols, catechins, and epicatechins. According to some aspects, the level of total flavanols may be either increased or decreased by about 10%-100%, 25%-75%, or about 40%-60% compared to *T. cacao*. According to other aspects, the level of catechins may be either increased or decreased by about 10%-100%, about 25%-75%, or about 40%-60% compared to *T. cacao*. According to still other aspects, the level of epicatechins may be either increased or decreased by about 10%-100%, about 25%-75%, or about 40%-60% compared to *T. cacao*.

In some aspects, hybrid seeds having any of the properties described above are used to make cocoa products. For example, hybrid seeds having decreased palmitic acid compared to *Theobroma cacao* and/or decreased theobromine compared to *Theobroma cacao* are used to prepare cocoa products.

In other aspects, the presence of tetramethyluric acid is used to confirm whether the seeds are a result of hybridization of *T. cacao*×*T. grandiflorum*. In other aspects, hybrid seeds having presence of tetramethyluric acid are used to make cocoa products.

Analysis of the genetic material of the seeds may also be carried out to confirm whether the seeds are a result of hybridization of the two parental plants. For example, DNA analysis of samples of cotyledons obtained from the seeds may be conducted to identify the presence or absence of specific markers. Specific SNPs may be selected, for example, based on their distribution across the chromosomes of the parents being crossed, in order to permit confirmation that hybridization has occurred throughout the genome. In some aspects, the presence or absence of one or more of the 22 SNP markers shown in FIGS. 20A and 20B is determined. In other aspects, the presence or absence of one or more of the 11 SNP markers shown in FIGS. 21A and 21B are determined.

In other aspects, the presence or absence of one or more (e.g., 2, 3, 4, 5, 6, 7, 8, or 9) of the following 9 markers are determined: w17s189(T/C), e0050s274(C/T), CIR211s1036 (T/A), w11s867(T/C), w8s204(T/C), c3s595(C/A), w3s41 (G/T), w8s131(T/C), w3s558(A/G). These SNPs are discussed in one or more of the following, each of which is hereby incorporated by reference: Borrone et al., Theor. Appl. Genet. 109 (3), 495-507 (2004); Pugh et al., Theor. Appl. Genet. 108 (6), 1151-1161 (2004); Kuhn et al., Tree Genetics & Genomes 6, 783-792 (2010); Livingstone et al., Mol Breeding (2011) 27:93-106; Kuhn et al., Tree Genetics & Genomes 8, 97-111 (2012). Information regarding these SNPs (e.g., NCBI accession numbers, primer/probe combination and sequences used for detecting the SNPs) is provided in Table 1 below. In particular, the SNPs can be identified, selected, screened, and/or detected using the primer and/or probe combinations described in Table 1.

TABLE 1

SNP Markers

| Loci Name | NCBI ref. | Marker Name | Linkage Group | Primer/Probe Combination | Allele | Fluorescent label | Sequence | Tm | %GC |
|---|---|---|---|---|---|---|---|---|---|
| WRKY 17 | EF173893 | w17s189 | 1 | Wrky17_189_F | | | TGATTACACTGTTACACCAACTTTAGACG (SEQ ID NO: 1) | 59.8 | 38 |
| | | | | Wrky17_189_R | | | ACGTGTAAAGAAGGAGGAAAACTTT (SEQ ID NO: 2) | 58.1 | 35 |
| | | | | Wrky17_189_t | T | VIC | TCTTGctGAGATATC (SEQ ID NO: 3) | 67 | 40 |
| | | | | Wrky17_189_c | C | FAM | TCTCTTGCcGAGATAT (SEQ ID NO: 4) | 67 | 44 |
| | CA797820 | e0050s274 | 3 | Est_0050_229_F | | | CTCAGGTTCCAACCATTGATTTAA (SEQ ID NO: 5) | 58.1 | 38 |
| | | | | Est_0050_229_R | | | CCGAGATCCCATGGTTAACAA (SEQ ID NO: 6) | 58.4 | 48 |
| | | | | Est_0050_229_c | C | FAM | AAGCTGCCAcGGAGT (SEQ ID NO: 7) | 67 | 60 |
| | | | | Est_0050_229_t | T | VIC | AAGCTGCCAtGGAGT (SEQ ID NO: 8) | 67 | 53 |
| WRKY 11 | AY331171 | w11s867 | 5 | Wrky17_867_F | | | AACTGTCAGCTGTCTCTCTTTCTTG (SEQ ID NO: 9) | 58.5 | 42 |
| | | | | Wrky17_867_R | | | CAGAACTGTGCATGCTTGAAGC (SEQ ID NO: 10) | 59.7 | 50 |
| | | | | Wrky17_867_t | T | VIC | CTAAATGAATCAtCCAAAGA (SEQ ID NO: 11) | 65 | 30 |
| | | | | Wrky17_867_c | C | FAM | AAATGAATCAcCCAAAGA (SEQ ID NO: 12) | 58.9 | 33 |
| WRKY 3 | AY331158 | w3s41 | 2 | w3s41_FW | | | AAAGGCAATCTTACCCAAGGT (SEQ ID NO: 13) | 58.9 | 45 |
| | | | | w3s41_RV | | | AAGAATGAACCACTTTGCAGTAGATAGT (SEQ ID NO: 14) | 58.1 | 36 |
| | | | | w3s41_pG | G | FAM | ATgCCcTggtTgt (SEQ ID NO: 15) | 65 | 57 |
| | | | | w3s41_pT | T | VIC | atGcccctGTTtgt (SEQ ID NO: 16) | 65 | 50 |
| WRKY 3 | AY331158 | w3s558 | 2 | w3s558_FW | | | GTTGTTGTTCTTGTTCAATTCGTATGA (SEQ ID NO: 17) | 58.2 | 35 |
| | | | | w3s558_RV | | | ATCAGGAATGCTCCAAAATAATCAA (SEQ ID NO: 18) | 58.9 | 32 |
| | | | | w3s558_pG | A | FAM | tgactACcttttatgTgAtCt (SEQ ID NO: 19) | 66 | 33 |
| | | | | w3s558_pT | G | VIC | TGACTgCCTTTTATGTGAT (SEQ ID NO: 20) | 66 | 37 |
| WRKY 8 | AY331165 | w8s131 (probe 119) | 9 | w3s131_FW | | | GCCCTGTCAAAAGAAGGTACTG (SEQ ID NO: 21) | 64.7 | 48 |
| | | | | w3s131_RV | | | TTACTCTTGCTTTCCATTTTCTAAGTG (SEQ ID NO: 22) | 64.1 | 33 |
| | | | | w3s131_pG | T | VIC | TTCTGAGGTATCATTCCCA (SEQ ID NO: 23) | 69 | 42 |

TABLE 1-continued

SNP Markers

| Loci Name | NCBI ref. | Marker Name | Linkage Group | Primer/Probe Combination | Allele | Fluorescent label | Sequence | Tm | %GC |
|---|---|---|---|---|---|---|---|---|---|
| | | | | w3s131_pT | C | FAM | TTCTGAGGCATCATTCC (SEQ ID NO: 24) | 71 | 47 |
| WRKY 8 | AY331165 | w8s204 | 9 | w3s204_FW | | | cacttagaaaatggaaagcaacagt (SEQ ID NO: 25) | 63.2 | 36 |
| | | | | w3s204_RV | | | acctagagccagatgatgaattgtatt (SEQ ID NO: 26) | 64.6 | 37 |
| | | | | w3s204_pG | T | VIC | ttccTgagacttgtacttga (SEQ ID NO: 27) | 68 | 40 |
| | | | | w3s204_pT | C | FAM | ttccCgagacttgtactt (SEQ ID NO: 28) | 68 | 44 |
| COS 3 (Tc_At1g44446) | XM007019015 | c3s595 | 8 | c3s595_FW | | | TGCTGGTGGCAAGAAGTATTATATTAG (SEQ ID NO: 29) | 58.1 | 37 |
| | | | | c3s595_RV | | | CAGATCCTCATTCAATACCTGTATCAA (SEQ ID NO: 30) | 58.6 | 37 |
| | | | | c3s595_pA | A | 6FAM | CTCTGCaTCATTGGT (SEQ ID NO: 31) | 66 | 47 |
| | | | | c3s595_pC | C | VIC | CTCTGCcTCATTGGT (SEQ ID NO: 32) | 67 | 53 |
| mTcCir211 | AJ566534 | CIR211s1036 | 8 | CIR211s1036_FW | | | ACCTTAATTTTATGGGAAACGAGT (SEQ ID NO: 33) | 58.4 | 36 |
| | | | | CIR211s1036_RV | | | CCAAACAAAATCTTAATGCACTGTG (SEQ ID NO: 34) | 58.7 | 36 |
| | | | | CIR211s1036_pT | T | VIC | AATCtGTGCTGACTGAT (SEQ ID NO: 35) | 67 | 41 |
| | | | | CIR211s1036_pA | A | 6FAM | CAATCaGTGCTGACTG (SEQ ID NO: 36) | 65 | 50 |

In order to conduct the SNP analysis, the genetic profile of the parent plants with respect to the SNPs of interest must first be evaluated. Preferred varieties of *T. cacao* and *T. grandiflorum* that may be used as parental plants are shown in FIGS. 18A-18B. Each parent preferably has a different allele for a selected SNP, and is homozygous, in order to allow the SNP to be used to assess hybridization. The genetic profile of the parent plants with respect to 22 SNPs are shown in FIGS. 20A and 20B. Progeny that are heterozygous at a given SNP for SNPs meeting these criteria have undergone some degree of hybridization. Examples of 81 different crosses performed using different varieties of *T. cacao* and *T. grandiflorum* as parent plants are provided in FIGS. 19A-19B, and the genetic profile of these crosses with respect to 11 SNPs are shown in FIGS. 21A and 21B. Examples of 12 different crosses and their genetic profiles with respect to 9 SNPs is shown in FIG. 22.

The seeds, and in particular the seeds selected after the chemical and/or genetic analysis, are planted into a suitable plant growth medium (e.g., as shown in FIG. 5). In a particular embodiment, the medium used in step (b) is a woody medium such as Woody Plant Medium (Lloyd and McCown's, 1981). However, any medium capable of supporting growth of the hybrid plants may be used.

The seeds are incubated in the growth medium at a suitable temperature, such as from 20-35° C., preferably from 25-32° C., more preferably from 27-30° C. According to some aspects, they may be maintained in a humid atmosphere, for example in an environment having at least about 50% relative humidity, at least about 70% relative humidity, or at least about 85% relative humidity. However, any conditions capable of supporting growth of the hybrid plants may be used in accordance with the invention.

Seeds are allowed to mature to plantlets under these conditions. Typically, this takes from 5-25 days, or, for example, from 10-15 days.

Figure 6:
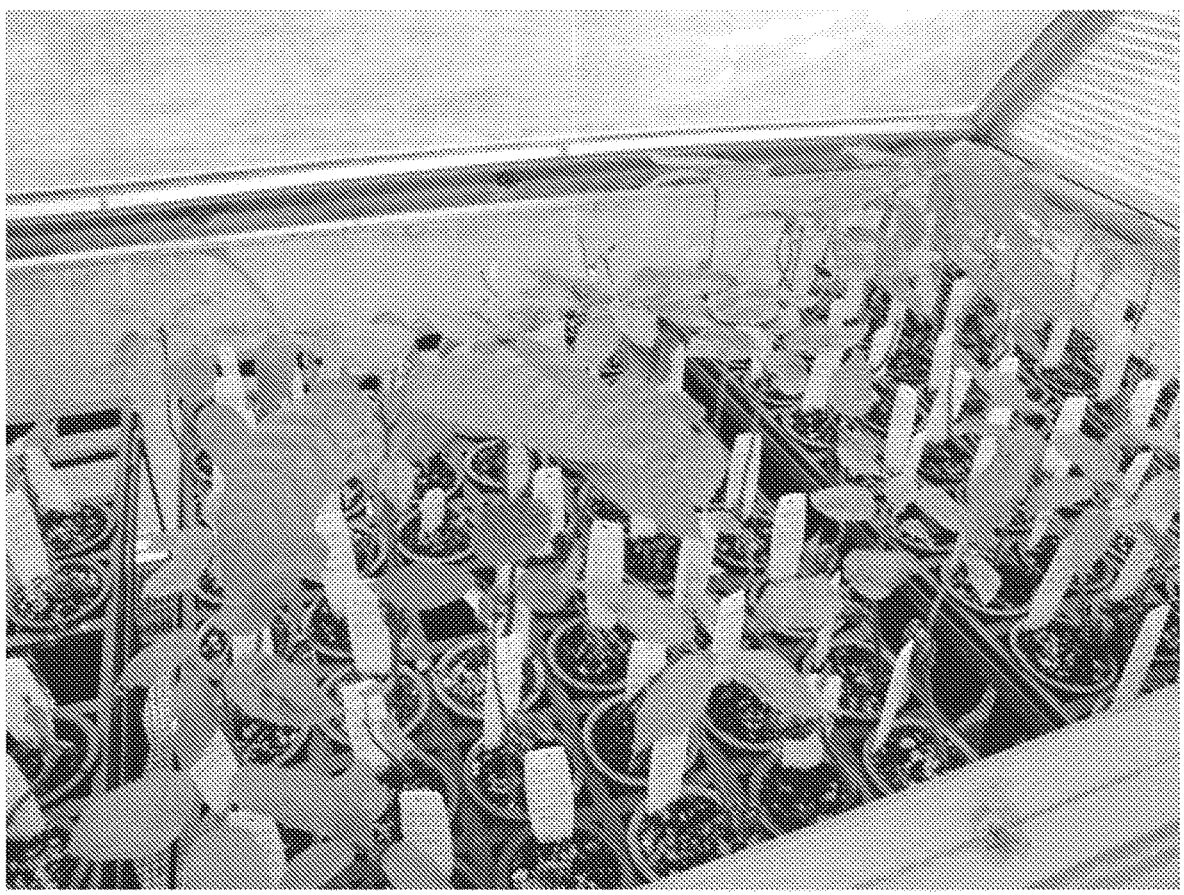
FIG. 6 is a photograph of young hybrid seeds being acclimated in a humid chamber.

According to other aspects of the invention, after the hybrid plantlets have matured, they may be held in a humid chamber with a high humidity, for example of at least 80% relative humidity and suitably at least 90% humidity to allow them to acclimatize (e.g., as shown in FIG. 6).

The plantlets are transferred to and grown in a suitable medium. According to some aspects of the invention, the medium comprises peat moss, coconut powder, perlite, and mixtures thereof. In other aspects, the medium comprises coconut powder and Carolina Soil (commercially sold; Substrate Carolina Standard CE=0.7 ms/cm+/−0.3; Composition: expanded vermiculite, sphagnum peat, agricultural lime, gypsum and fertilizer dashes (NPK), pH=5.5+/−0.5)).

The plantlets may be grafted to other plants. For example, suitable plants to which the hybrid plantlets may be grafted include *Theobroma grandiflorum* (e.g., as shown in FIGS. 8A-8B) and *Theobroma cacao*. In several aspects, the hybrid plantlets are grafted onto *T. cacao* VB-1151 rootstock. In a particular aspect, the hybrid plantlets from P-7B×MCSG-122 or NA-45×MCSG-122 are grafted onto a *T. cacao* rootstock, such as VB-1151.

Figure 7:
FIG. 7 is a photograph of a flower produced by hybrid plant MCGH-067-002-31.

The hybrid plants described herein may be grown to maturity and allowed to produce flowers (e.g., as shown in FIG. 7), fruit/pods, and seeds for use in further aspects of the invention. The mature flowers can be grafted onto other plants (e.g., *Theobroma cacao*) or specific rootstock (e.g., VB-1151) as discussed in the preceding paragraph.

Analysis of the genetic material of the hybrid plants may be carried out at a mature stage by analyzing samples of the plant, such as leaf, stem, root, or flower tissue, to confirm whether the hybrid plants are a result of hybridization of the two parental plants. For example, DNA analysis of samples such as leaf samples obtained from the plants may be conducted to identify the presence or absence of specific markers discussed above with respect to the seeds.

Methods of producing *T. cacao* and *T. grandiflorum* hybrid plants and parts thereof, as well as, hybrid products, such as seed obtained by crossing *T. cacao* and *T. grandiflorum*, are provided. In several aspects, the methods comprise crossing a variety of *T. cacao* and *T. grandiflorum* and obtaining seeds therefrom, and selecting seeds and/or plants resulting from the cross. The seeds and/or plants may be selected based on the characteristics described herein, such as whether they possess decreased palmitic acid as compared to *T. cacao*; decreased theobromine compared to *T. cacao*; the presence of tetramethyluric acid; and/or one or more of the following SNP markers: w17s189(T/C), e0050s274(C/T), CIR211s1036(T/A), w11s867(T/C), w8s204(T/C), c3s595(C/A), w3s41(G/T), w8s131(T/C), w3s558(A/G), and any combination thereof. In other aspects, methods for identifying, selecting, screening and/or confirming *T. cacao* and/or *T. grandiflorum* hybrid plants or plant products, such as seeds obtained from crossing *T. cacao* and *T. grandiflorum*, based on one or more of the above-mentioned characteristics are also provided.

In other embodiments, methods for producing a hybrid plant of *T. cacao* and *T. grandiflorum* are provided, which comprises (a) crossing a variety of *Theobroma cacao* and a variety of *Theobroma grandiflorum* and obtaining hybrid seed therefrom; (b) sowing hybrid seeds obtained in a growth medium and incubating them in a growth room until plantlets have been formed; (c) transferring plantlets to a suitable substrate; and (d) optionally grafting hybrid plantlets obtained onto a plant. In other embodiments, after step (a), and before step (b), a sample of seed is removed and the chemical composition and/or genetic makeup is analyzed. In other embodiments, only seeds that possess certain characteristics, such as the above-mentioned characteristics and/or SNP markers, progress on to step (b). Hybrid plants produced by these processes are also provided.

In other aspects, hybrid plants obtained from any of the crosses described herein are crossed with another plant. In some aspects, the hybrid plants are backcrossed with one of its parents (*T. cacao* or *T. grandiflorum*), and seeds are obtained. In other aspects, hybrid plantlets are grafted onto rootstock, as discussed above, and the resulting plant is crossed with another plant or backcrossed with one of its parents (*T. cacao* or *T. grandiflorum*).

Methods for removing the fruit from a *Theobroma cacao* and *Theobroma grandiflorum* cross and processing it into a cocoa product are also provided. In accordance with such further aspects, there is provided a hybrid plant-derived product, preferably seeds obtained from crossing *T. cacao* and *T. grandiflorum*, which comprise fatty acids. The seeds have a fatty acid profile that is altered as compared to the fatty acid profile of seeds produced by the parents from which the hybrids were obtained. These fatty acid profiles described herein are advantageous because saturated fatty acids, such as palmitic acid, may be associated with increased risk of cardiovascular disease, and unsaturated fatty acids, such as linoleic acid, may be useful in reducing LDL cholesterol and the risk of cardiovascular disease. Thus, the hybrid plants, or seeds obtained from crossing *T. cacao* and *T. grandiflorum*, described herein provide a particularly suitable starting material for the production of foodstuffs possessing the fatty acid, flavanol, and alkaloid profiles of the plant products from which they are made, such as confectionaries, including, but not limited to chocolate and cocoa-containing products.

The processing techniques used to prepare cocoa products include partially or fully depulping the fruit of the plant (e.g., from the cross of *T. cacao* and *T. grandiflorum*), fermenting the beans using microbiological processes or chemical processes, drying the beans and exposing them to the sun or an artificial dryer, including, but not limited to, a Samoan dryer, Buttner dryer, and a platform dryer.

According to some aspects, the dried beans may be further roasted and winnowed to generate nibs that are converted to cocoa liquor or cocoa butter. Cocoa liquor may be converted to cocoa powder. The liquor, which still contains the cocoa butter, may be mixed with sugar or other natural or synthetic sweetening substances. In some aspects, the resulting mixture may be in the form of a paste.

The paste may be refined, optionally by means of a roller system, in order to generate smaller particle sizes within the paste. According to further aspects, milk solids may be added, and the mixture then further processed to a milk crumb. This mixture may be mixed in a conche, optionally with cocoa butter and emulsifier. The paste and crumb may also be mixed with cocoa butter and emulsifier in a conche. The conche used for the mixing includes, but is not limited to, a Frissee conch, a Tourell conche, Macintyre refiner/conche, and a wiener process.

The end product of this process of preparing, and optionally refining and further processing the paste is an edible cocoa containing product, including, but not limited to, chocolate, compound chocolate, or a chocolate-like substance.

Presently-preferred cocoa products that may be produced using the fruit from the plants propagated in accordance with methods herein (e.g., fruit from cross of *T. cacao* and *T. grandiflorum*) include cocoa liquor, chocolate, compound chocolate, chocolate-like substance, cocoa powder, and cocoa butter. Cocoa-containing products obtained by the processes described above are also provided.

In some aspects, cocoa products having a higher melting temperature and/or higher crystallization temperature than *T. cacao* products are provided. In other aspects, heat-resistant cocoa products are provided.

EXAMPLES

Various embodiments of the invention will now be particularly described by way of examples. However, it will be apparent to one skilled in the art that the specific details are not required in order to practice the invention. The following descriptions of specific embodiments are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

Example 1

This example provides *T. cacao* and *T. grandiflorum* hybrids and hybrid products, such as seed obtained from crossing *T. cacao* and *T. grandiflorum*, as well as, chemical and genetic characteristics of such hybrids and hybrid products.

1. Choice of Progenitors

The pollen donors were selected among plants from the *T. grandiflorum* collection held at MCCS. The female plants were selected from the MCCS *T. cacao* germplasm collection based on the diversity panel of cacao genetic diversity.

FIGS. 18A-18B include the varieties selected for use in developing the crosses.

2. Pollinations

The pollinations were performed manually, by covering the mother flower with a polyethylene transparent tube for 24 hours, prior to bud opening (FIG. 2A). Then flowers from *T. grandiflorum* were collected (FIG. 2B) and their pollen was rubbed against the pistil of the female *T. cacao* flower (FIG. 2C). The pollinated flower was covered again for 24 hours with the same tube.

After 24 hours, the success of pollination was checked and this was repeated subsequently after 5, 15, and 30 days. An example of a flower following successful pollination is shown in FIG. 2D.

3. Collection of Hybrid Seeds

The pollinated flowers were allowed to develop and mature pods were harvested between 140 and 160 days after pollination, as shown in FIG. 3A. After harvest, they were taken to the laboratory, cleaned with bleached water, flamed and opened under the laminar flow hood. The seeds were taken out with sterile forceps and the testa of each seed was peeled off, and the resulting seeds are shown in FIG. 4A-4D.

The resultant hybrid seeds were then sown in Woody Plant Medium (Lloyd and McCown's, 1981) media the composition of which is set out in Table 1, and placed in a growth room at about 27-30° C., and 70% RH, as shown in FIGS. 3B-C.

TABLE 1

| WPM medium composition | |
|---|---|
| WPM Solution I | |
| $NH_4NO_3$ | 20 g/L |
| $Ca(NO_3)_2\ 4H_2O$ | 27.8 g/L |
| WPM Solution II | |
| $K_2SO_4$ | 49.5 g/L |
| WMP Solution III | |
| $CaCl_2\ 2H_2O$ | 19.2 g/L |
| WPM Solution IV | |
| $H_3BO_3$ | 0.62 g/L |
| $KH_2PO_4$ | 17 g/L |
| $Na_2MoO_4\ 2H_2O$ | 0.025 g/L |
| MS Solution II | |
| $MgSO_4\ 7H_2O$ | 37 g/L |
| $MnSO_4\ H_2O$ | 2.23 g/L |
| $ZnSO_4\ 7H_2O$ | 0.86 g/L |
| $CuSO_4\ 5H_2O$ | 0.0025 g/L |
| MS solution IV | |
| $Na_2$ EDTA | 3.73 g/L |
| $FeSO_4\ 7H_2O$ | 2.78 g/L |
| Final Concentration (mg/L) | |
| $NH_4NO_3$ | 400 |
| $Ca(NO_3)_2\ 4H_2O$ | 556 |
| $K_2SO_4$ | 990 |
| $CaCl_2\ 2H_2O$ | 96 |
| $H_3BO_3$ | 6.2 |
| $KH_2PO_4$ | 170 |
| $Na_2MoO_4\ 2H_2O$ | 0.25 |
| $MgSO_4\ 7H_2O$ | 370 |
| $MnSO_4\ H_2O$ | 22.3 |
| $ZnSO_4\ 7H_2O$ | 8.6 |

TABLE 1-continued

| WPM medium composition | |
|---|---|
| CuSO$_4$ 5H$_2$O | 0.25 |
| FeNaEDTA 3H$_2$O | 42.1 |

4. Chemical Analysis

In some instances, after collection of the hybrid seeds and before sowing, a sample comprising approximately ⅓ of a cotyledon was cut from the seed as illustrated in FIG. 5 in order to determine the chemical composition of the hybrid seeds. The sample was first freeze-dried, and chemical analysis was performed. The samples were analyzed for fatty acids, flavanols, and alkaloids.

The fatty acid composition (e.g., palmitic acid) was determined using capillary GC. The fats were transesterified to their respective fatty acid methyl esters (FAMEs) with methanolic tetramethylammonium hydroxide. The FAMEs were then separated on a HP Innowax capillary column with FAME composition determined by area normalization. Quantitative determination was accomplished using external standard calibration. External standard typically used is Nu-Chek GLC Reference Standard 68C. One point calibration curves were constructed for all components, thus accounting for differences in relative response factors of fatty acids.

Cocoa flavanol content was determined using normal phase HPLC. Lyophilized cocoa bean powder was extracted with hexane to remove the lipid components prior to extraction of the flavanols/procyanidins. Next, flavanols/procyanidins (DP1-10) were extracted from defatted samples with an acidified acetone/water solvent system. The extracts were then passed through a solid phase extraction (SPE), filtered and transferred to chromatographic vials for normal phase HPLC analysis. Quantification was accomplished with the external standard approach, and a calibration curve was constructed for each flavanol/procyanidin fraction. The values reported for total flavanol and procyanidin content of the sample is the sum of the quantities determined for each oligomeric fraction (DP1-10).

Alkaloid levels (theobromine, caffeine and TMUA) were determined using reverse phase HPLC with UV detection at 274 nm. Lyophilized bean powder samples were prepared by dissolution in hot (>95° C.) water, filtered and analyzed by HPLC. External standard calibration was employed for quantitative determination of the alkaloids, and NIST baking chocolate as used as a secondary standard to evaluate and ensure method/system performance.

The distribution of palmitic acid in seeds obtained from 2009 to 2013 from 37 different crosses as shown in FIG. 9, was analyzed using the Shapiro-Wilk test. The variable "Length" in FIG. 9 indicates the number of seeds analyzed for each cross. 4 crosses could not be submitted to the test, because the number of samples (seeds) was <3. The average (i.e., mean) palmitic levels of many hybrids are significantly lower than the palmitic acid level of *T. cacao* (see FIG. 1).

Figure 10:
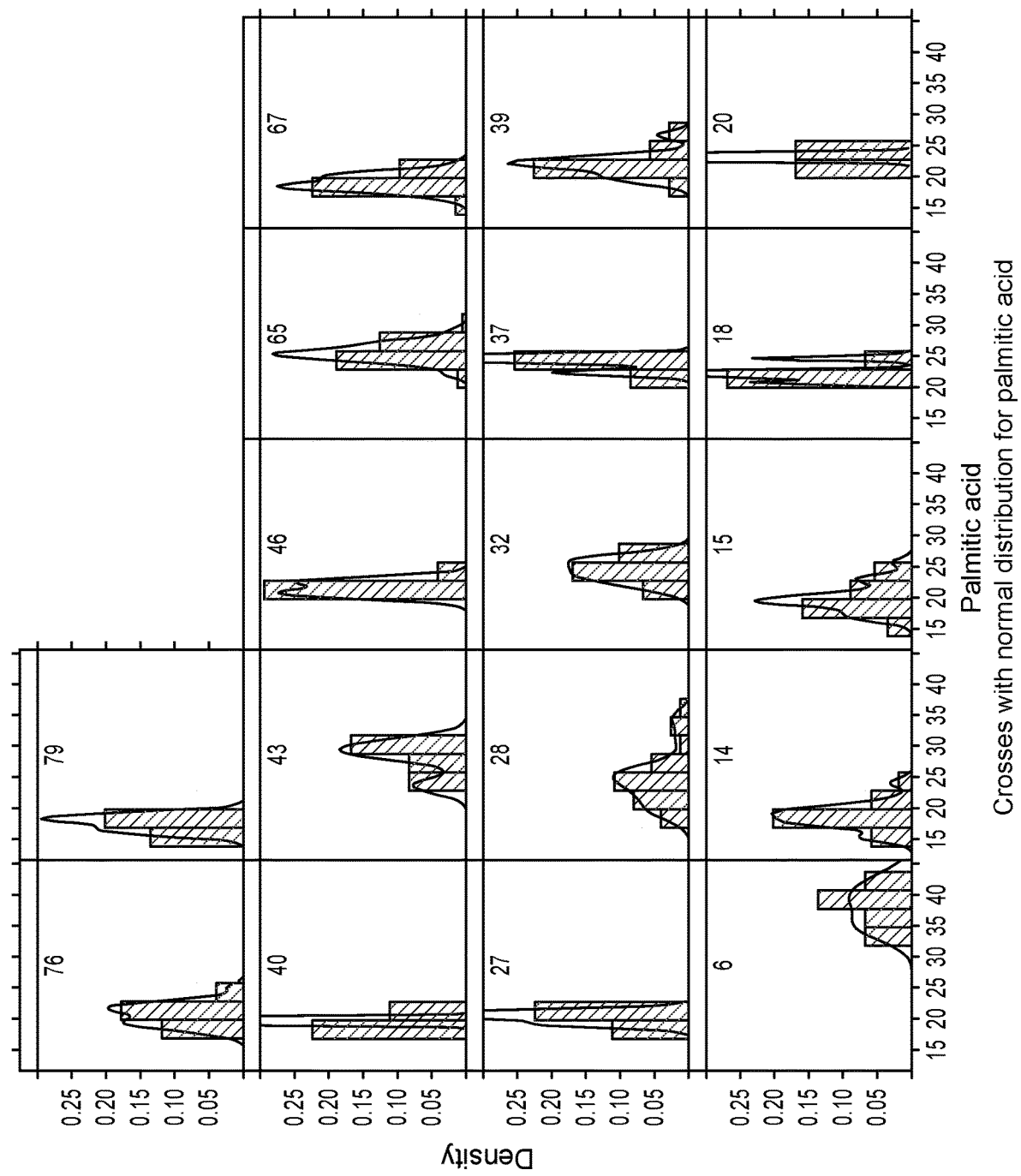
FIG. 10 is a series of histograms showing hybrid plants having normal palmitic acid distribution. The cross number is shown at the top of each graph, the x-axis corresponds to the percentage of palmitic acid, and the y-axis corresponds to the density (or frequency) of values.
Figure 11:
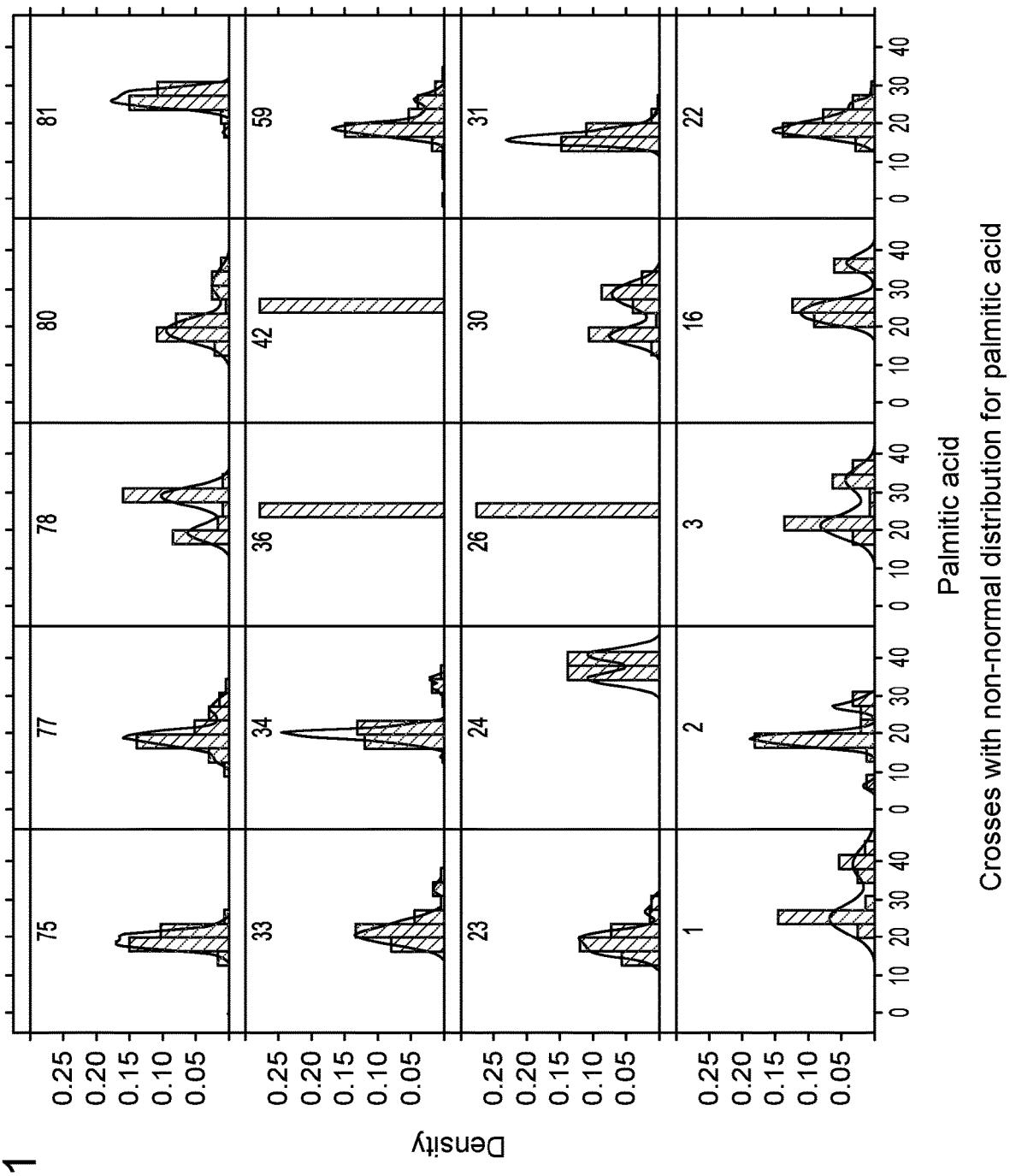
FIG. 11 is a series of histograms showing hybrid plants having non-normal palmitic acid distribution. The cross number is shown at the top of each graph, the x-axis corresponds to the percentage of palmitic acid, and the y-axis corresponds to the density (or frequency) of values.

Histograms showing the distribution of palmitic acid in hybrid seeds of the crosses, both normal and non-normal, are found in FIGS. 10-11. The palmitic levels of these hybrids are significantly lower than the palmitic acid level of *T. cacao* (see FIG. 1).

In 2012 and 2013, the methyxantines from the seeds were analyzed, in order to help to confirm the interspecific crosses. 957 samples were analyzed in 2012, and 678 samples in 2013 (only the samples with presence of tetramethyluric acid were analyzed for palmitic acid content).

Figure 12:
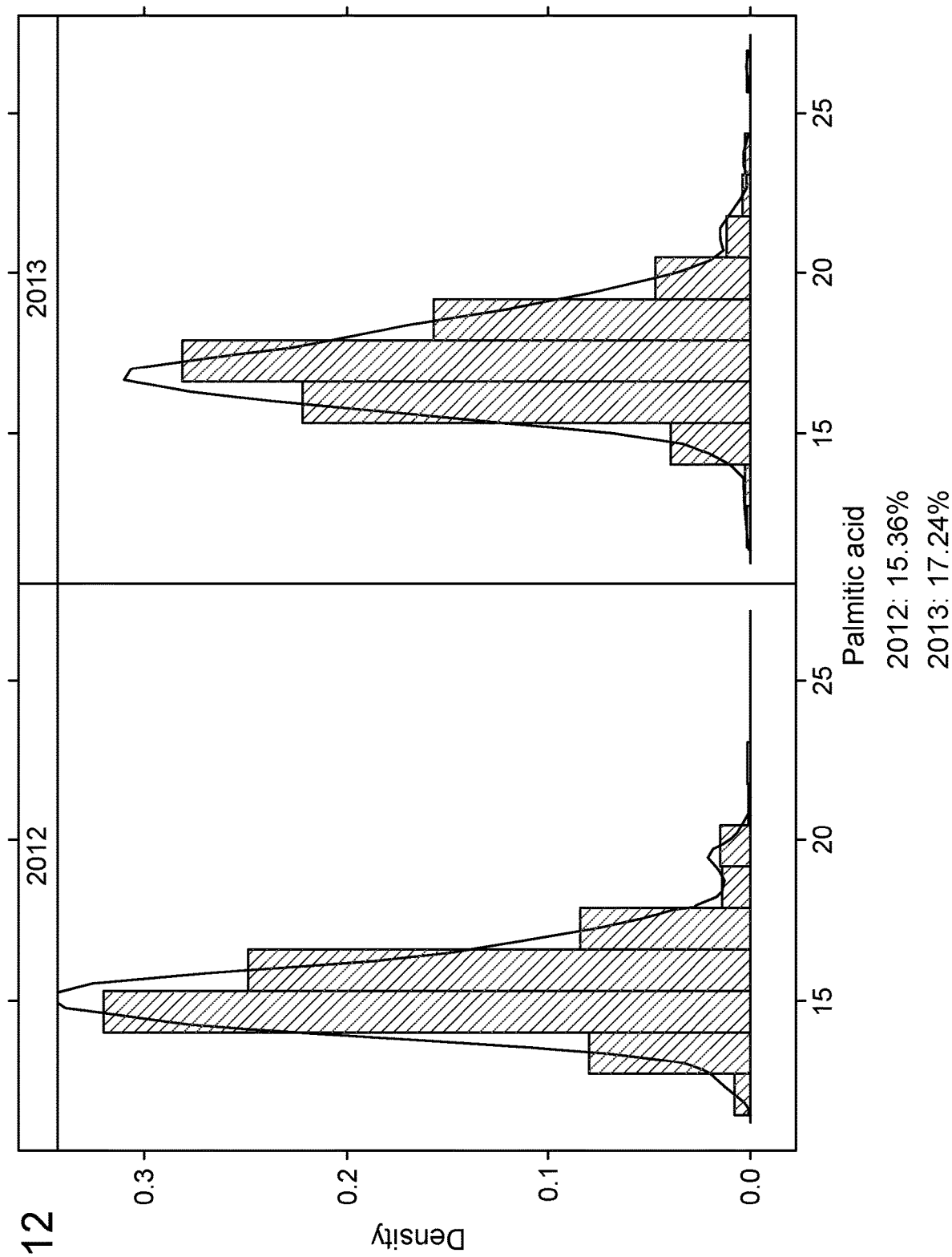
FIG. 12 is a histogram for cross 31 (corresponding to NA-45×MCGS-122), showing a normal distribution for palmitic acid exhibited by specimens collected in 2012 and 2013.

The palmitic acid, tetramethyluric acid, theobromine, and caffeine contents of the seeds obtained in 2012-2013 for NA-45×MCGS-122, are reported in FIGS. 12-15. FIG. 12 shows that the distribution of palmitic acid is normal and that the average is 15.36% in 2012, and 17.24% in 2013, which is lower than the known levels of *T. cacao* (see FIG. 1).

Figure 13:
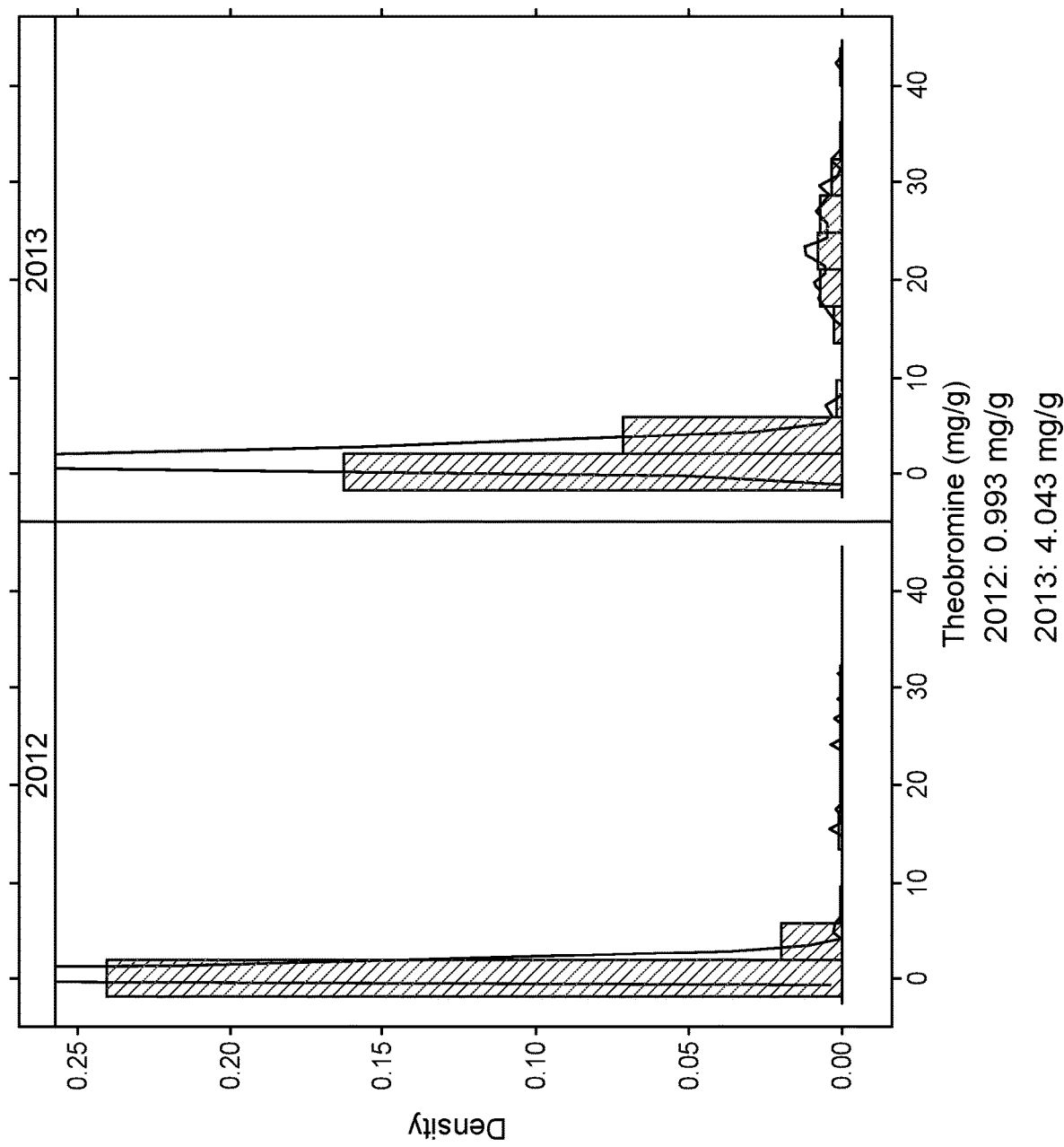
FIG. 13 is a histogram for cross 31, showing the distribution for theobromine exhibited by specimens collected in 2012 and 2013.

FIG. 13 shows that a normal distribution of theobromine and had an average of 0.993 mg/g in 2012, which is lower than *T. cacao*. In 2013, this average is 4.043 mg/g and a second peak of values in the range of 20-30 mg/g is observed. This elevated level theobromine is due to the fact that the cross generated several, non-hybrid seeds.

Figure 14:
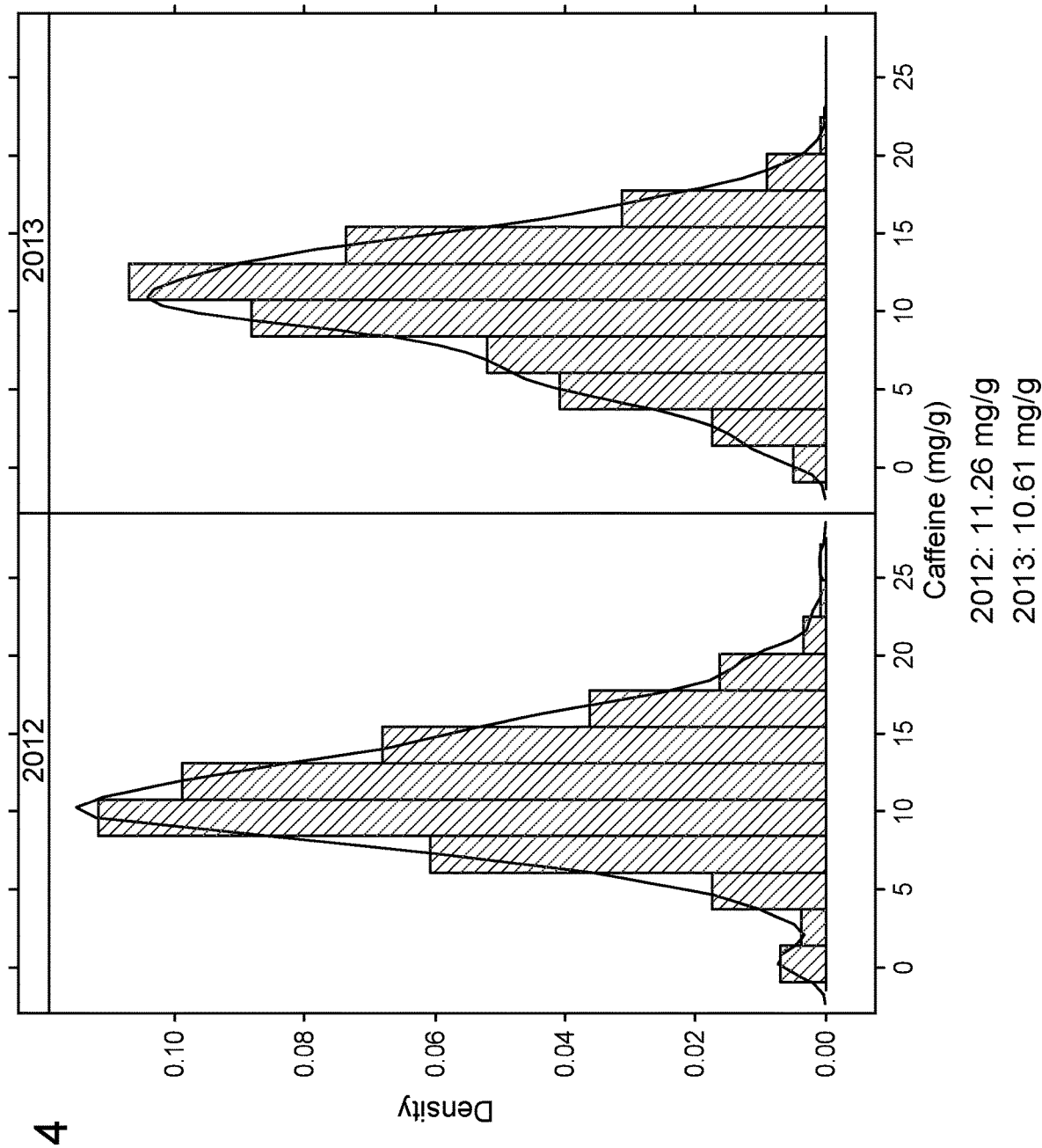
FIG. 14 is a histogram for cross 31, showing a normal distribution for caffeine exhibited by specimens collected in 2012 and 2013.

FIG. 14 shows that a normal distribution of caffeine and that the average is 11.26 mg/g in 2012, and 10.61 mg/g in 2013, which is higher than the known levels of *T. cacao*.

Figure 15:
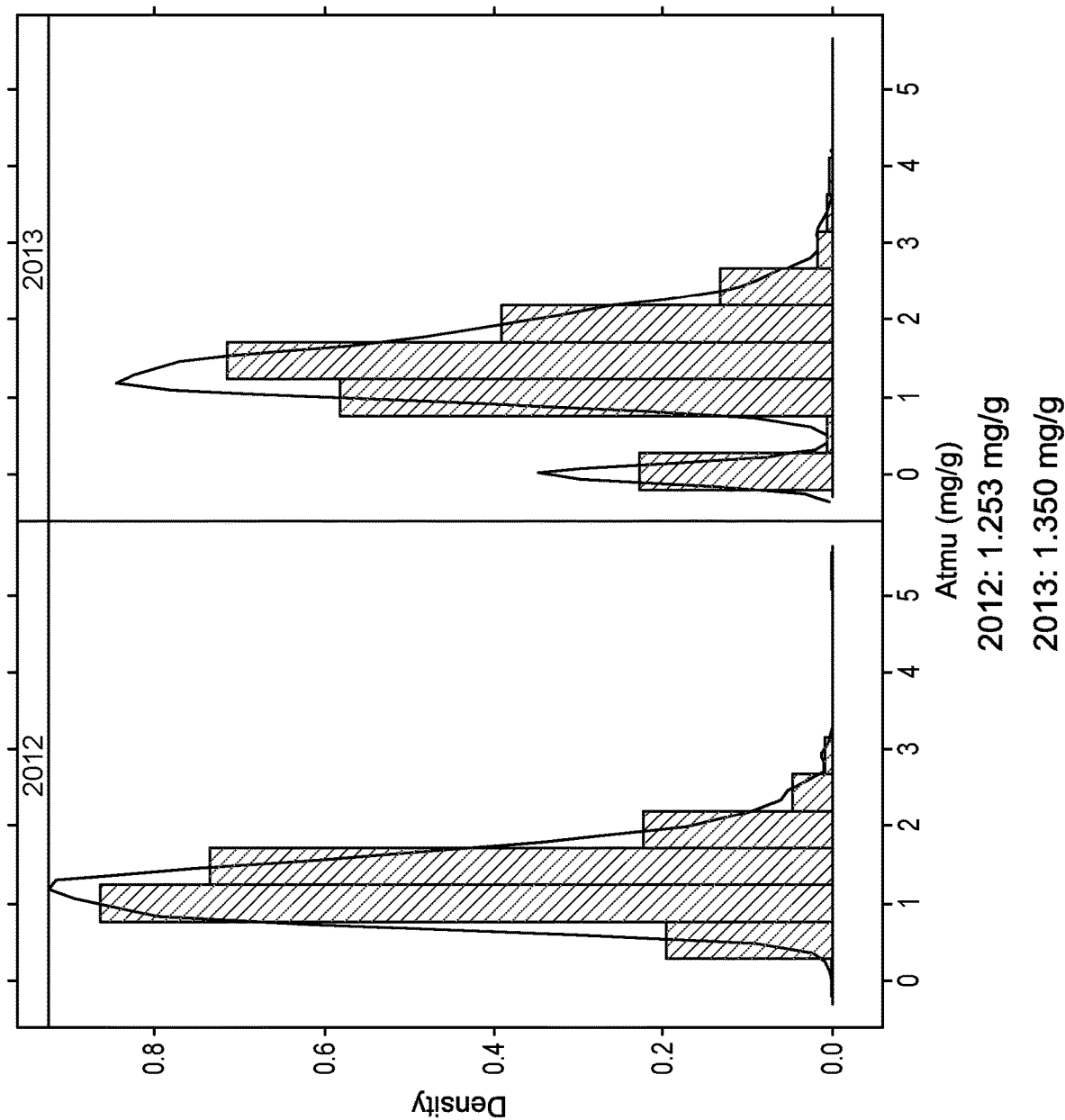
FIG. 15 is a histogram for cross 31, showing the distribution for tetramethyluric acid (TMUA) exhibited by specimens collected in 2012 and 2013.

FIG. 15 shows that the distribution of tetramethyluric acid (TMUA) is normal and, in 2012, all of the progeny were hybrids since all of the hybrids had the presence of TMUA. On the other hand, in 2013, there were several putative hybrids with TMUA levels similar to *T. cacao* (zero TMUA), and thus these progeny were not considered true *T. cacao×T. grandiflorum* hybrids (see above discussion regarding theobromine).

In addition, separate plants were analyzed for total cocoa flavanol content, as well as catechins and epicatechins, and the results are reported in FIGS. 16-17.

5. Growth of Hybrid Seeds

After 10-15 days in the growth room, hybrid plantlets were weaned in a humid chamber developed to keep high RH rates (100%) until they were acclimated (FIG. 6). They were then planted in a substrate made of peat moss, coconut powder and perlite.

The height of the young seedlings as well as the number of leaves was monitored every month. Their appearance was also recorded at this time. Many of the plants had a stunted growth and high mortality rate. However, depending on the specific *T. cacao×T. grandiflorum* combination some plants survived and reached various heights. For example, some of the smallest hybrids with *T. grandiflorum* appearance have a height between 16 cm (MCGH-023-037-07) and 22 cm (MCGH-031-020-16), whereas some of the tallest hybrids with *T. grandiflorum* appearance are between 64 cm (MCGH-023-013-02) and 85 cm (MCGH-023-014-03). All hybrids with *T. cacao* appearance develop as regular cacao and are already between 180 cm (MCGH-023-017-03) and 260 cm (MCGH-059-014-12) tall. The hybrids with *T. cacao* appearance also produced pods. All of these hybrids are about five years old.

Some plants produced flowers as shown in FIG. 6. The flower shares characteristics of the two species used for hybridization, i.e., in this particular case flowers with the appearance of *T. grandiflorum* but smaller (still bigger than *T. cacao*) and with a pedicel similar to cacao flowers.

6. DNA Analysis

Leaf discs of the hybrid plants were collected and DNA extraction carried out with a DNeasy Plant Mini Kit (Qiagen).

Genotyping was carried out using Single Nucleotide polymorphism markers (SNPs) developed for *T. cacao* (Kuhn et al. 2010).

51 clones of *T. cacao* and 25 clones of *T. grandiflorum* were analyzed in order to characterize the 81 crosses between *T. cacao* and *T. grandiflorum*, and 22 SNPs (Single Nucleotide Polymorphism) were used for the initial analysis (see FIGS. 20A and 20B). Leaf discs of the hybrid plants were collected and DNA extraction carried out with a DNeasy Plant Mini Kit (Qiagen). Of these, 11 SNPs were selected (see FIGS. 21A and 22B), and, subsequently, 9 SNPs were selected (shown in FIG. 22).

In one example, illustrated in FIG. 22, 9 SNPs, distributed over six different chromosomes, were used in analyzing the offspring of 12 crosses (86 analyzed individuals), including crosses from 7 different *T. cacao* mother plants, and 5 different *T. grandiflorum* pollinator plants. The highlighted SNPs were useful in confirming that hybridization took place. For example, in cross 15 (NA-45×MCSG-36), the following five SNPs were useful in determining hybrids: w17s189(T/C), e0050s274(C/T), CIR211s1036(T/A), w11s867(T/C), and w8s204(T/C). In a particular example, one offspring from cross 15, was heterozygous for three of the five SNPs (w17s189(T/C), e0050s274(C/T), and w11s867(T/C)), i.e., the offspring had one allele from each parent at the specific nucleotide position. Accordingly, one or more of the SNPs shown in FIG. 22 can be used in determining and/confirming *T. cacao*×*T. grandiflorum* hybrids.

7. Grafting of Hybrids

Some of the plantlets were grafted onto a *T. grandiflorum* rootstock, others onto a *T. cacao* rootstock. The plants developed well and were planted in the field, as shown, for example, in FIGS. 8A (MCGH-031-011-36), and 8B (MCGH-023-009-11). In this particular case, the hybrids were grafted onto a *T. grandiflorum* rootstock. Flowering of some of the hybrids has been attained, as shown, for example, in FIG. 7 (MCGH-067-002-31).

Example 2

Figure 23:
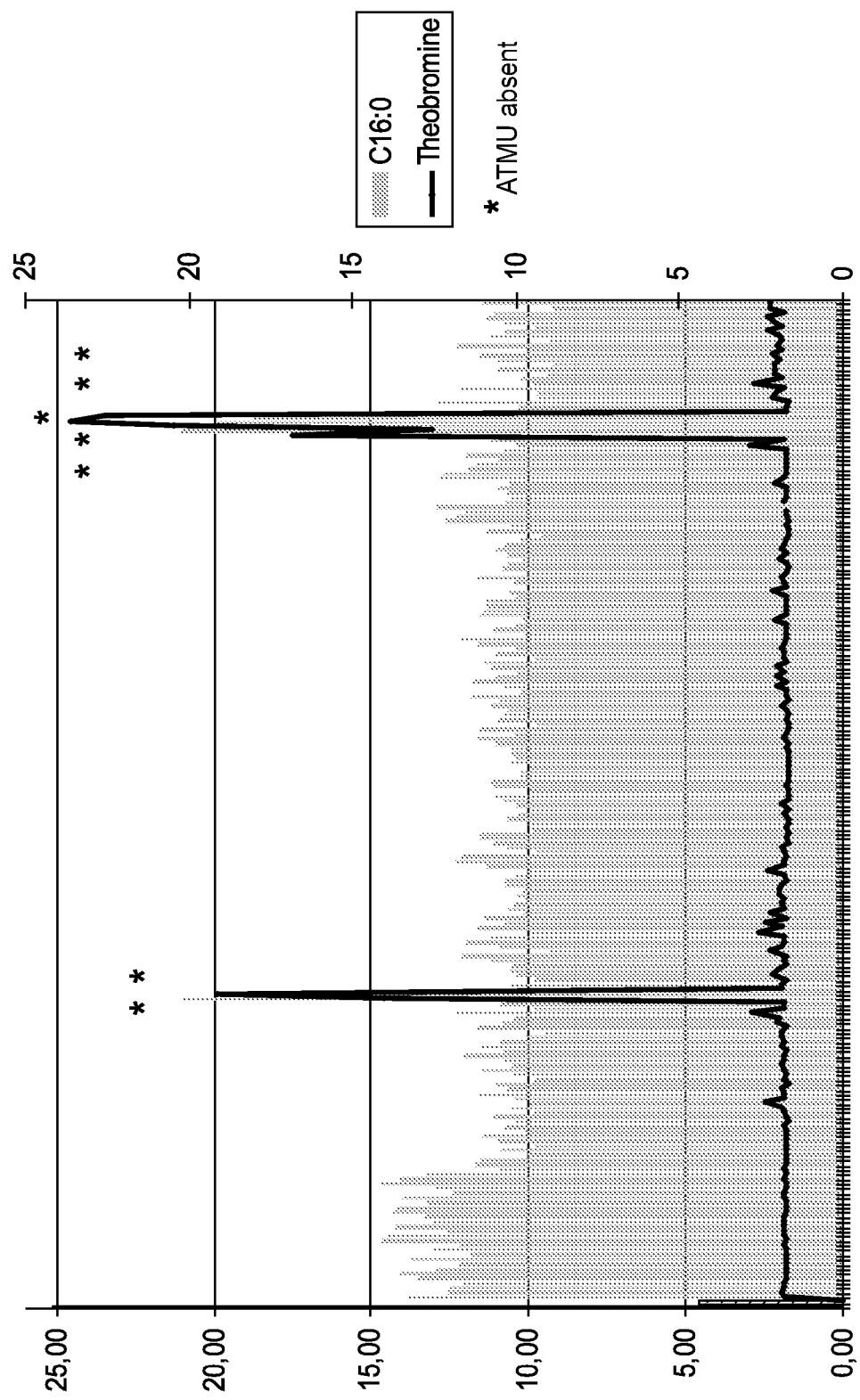
FIG. 23 is a graph showing palmitic acid (C16:0) (bars) and theobromine (lines) levels, and the presence or absence of tetramethyluric acid (TMUA) for NA-45×MCGS-122 crosses.

In 2010, the palmitic acid, tetramethyluric acid, and theobromine content of seeds from cross 31 (NA-45×MCGS-122) were analyzed using the methods described above. Ten pods and 211 seeds where collected. The results are shown in FIG. 23. The data shows that there is a correlation between palmitic acid, tetramethyluric acid, and theobromine content. Specifically, low palmitic acid levels are associated with low theobromine content and the presence of tetramethyluric acid. On the other hand, high palimitic acid levels are associated with higher theobromine levels and the absence of tetramethyluric acid. Accordingly, when there is no TMUA, low (e.g., less than 5 mg/g) theobromine, the individuals present low (e.g., less than 15%) palmitic acid.

Example 3

This example compares cocoa liquor obtained from seeds of *T. cacao*×*T. grandiflorum* hybrids and non-hybrids, a standard *T. cacao* plant (Low Roast West African-ELZ), and a *T. grandiflorum* plant.

Micro-Fermentation

Micro-fermentation of mature pods from NA-45×MCSG-122, EET400×MCSG46, and NA45×MCSG-46 were carried as follows. Pods were broken 1 day after harvest outside the laboratory and the bean content carefully removed and placed in individual nylon nets that are then sealed inside zip lock bags. Simultaneously, freshly prepared pulp were prepared and transferred to a covered jar at ambient temperature for about 1-3 hours in order to initiate its fermentation. Each bag containing the beans was then transferred to the laboratory where 5 mL of the freshly fermented pulp was added to the zip lock bag. The bags were incubated at controlled temperatures. On the second and fourth day, the sweatings of the each zip lock bag were removed and discarded. After fermentation, the beans were sun dried to a moisture content of 7 to 8%. After drying the beans from each individual bag, they were stored in jute bags. The beans for *T. cacao* plant (Low Roast West African-ELZ) and the *T. grandiflorum* plant were purchased commercially and thus already fermented.

Following drying, ⅓ of the seed was removed, lyophilized (freeze dried) and analyzed for palmitic acid (C 16:0) using capillary GC, and theobromine and TMUA content using reverse phase HPLC, as discussed above.

Based on palmitic acid content, the beans were divided into the following 8 groups (or bands):

Band 1 8.38-9.99% C16:0
Band 2 10.00-10.99% C16:0
Band 3 11.01-11.99% C16:0
Band 4 12.00-12.98% C16:0
Band 5 13.03-13.99% C16:0
Band 6 14.26-15.37% C16:0
Band 7 17.65-19.43% C16:0
Band 8 19.62-22.07% C16:0

Figure 24:
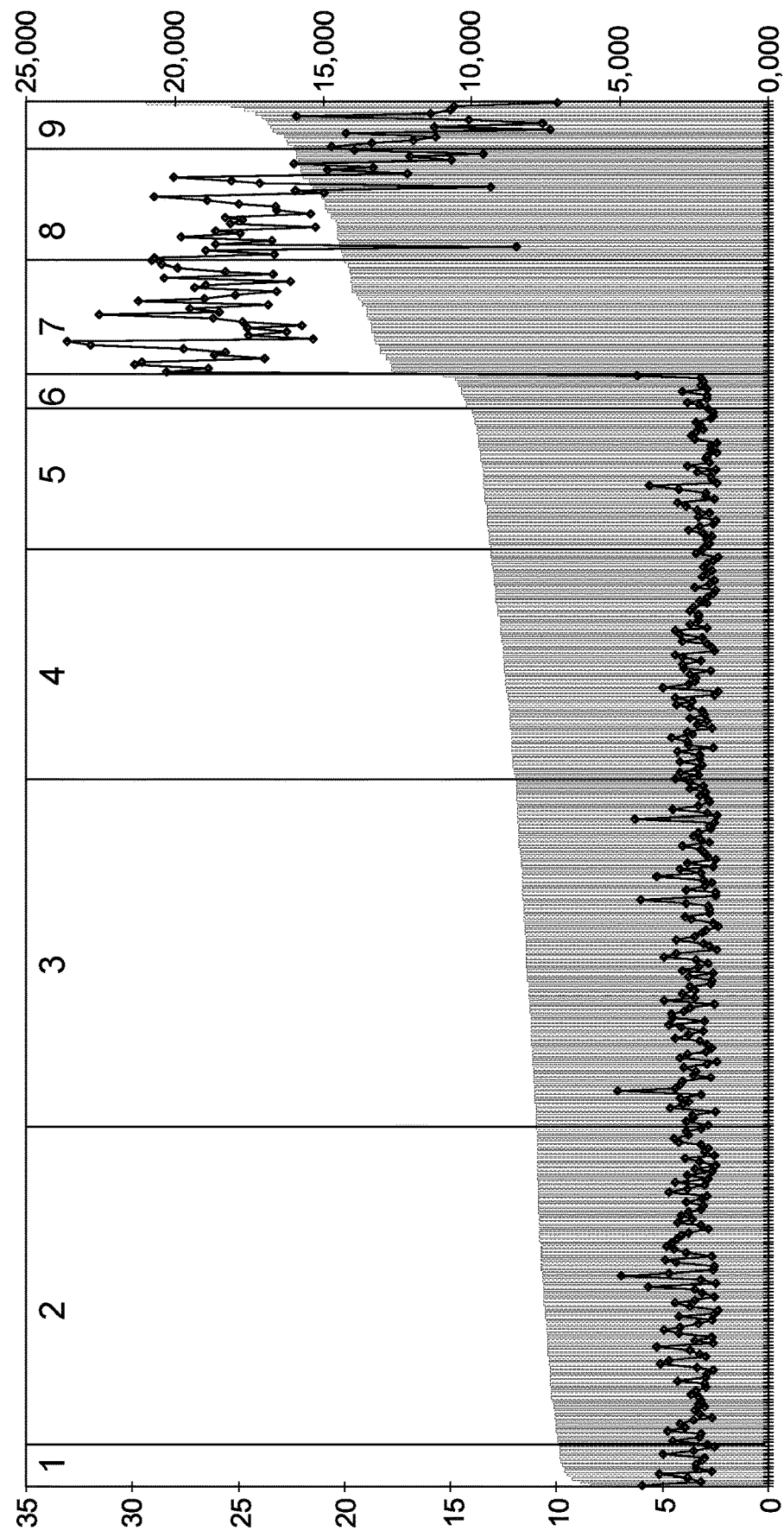
FIG. 24 is a graph showing palmitic acid (bars) and theobromine (lines) levels for collections of seeds from the following crosses: NA-45×MCSG-122, EET400×MCSG-46, and MA-45×MCSG-46.

These groups are also shown in FIG. 24. Theobromine levels are depicted as lines with specific data points, whereas palmitic acid levels are depicted as colored sections (or bars) in each band. It was determined, based on the low palmitic acid and theobromine levels, that the beans in bands 1-6 are hybrids. On the other hand, based on the higher palmitic acid and theobromine levels, the beans in bands 7 and 8 are not hybrids.

Liquor Making Procedure

To prepare cocoa liquor, the beans were placed in stainless steel trays and roasted in a Binder oven at 121° C. for 21 min. The beans were the cooled at room temperature and broken so that the nibs were easily separated from the shell in a portable winnower. Then, they were hand-picked to remove all of the shell. A total of 35 g of nibs was then milled in a Restch RM200 mill for 30 min. Finally, the liquor was transferred to a tube and stored at −20° C. for analyses.

Palmitic acid (C 16:0) and theobromine levels of liquors from seeds of hybrids (bands B1-B6), non-hybrids (bands B7-B8), *T. cacao*, and *T. grandiflorum* were analyzed. Palmitic acid was measured as a percentage of the total concentration of fatty acids, and theobromine was measured in mg/g. The results are shown below:

|  | B1 | B2 | B3 | B4 | B5 | B6 | B7 | B8 | Tc | Tg |
|---|---|---|---|---|---|---|---|---|---|---|
| C16:0 | 14.03 | 14.6 | 15.52 | 16.52 | 17.8 | 18.35 | 24.51 | 26.21 | 25.8 | 6.49 |
| Theo | 0.07 | 0.06 | 0.08 | 0.05 | 0.04 | 0.04 | 0.99 | 0.99 | 1.13 | 0 |

The results show that liquor from seeds of *T. cacao*×*T. grandiflorum* crosses have lower palmitic acid levels compared to *T. cacao*, and lower theobromine levels compared to *T. cacao*.

The melting temperature, crystallization temperature, and melt profiles were also analyzed according to Campos R.

(2005) Experimental Methodology, in Fat Crystal Networks, Editor Alejandro G. Marangoni, Marcel Dekker, USA. pp. 267-348.

Figure 25A:
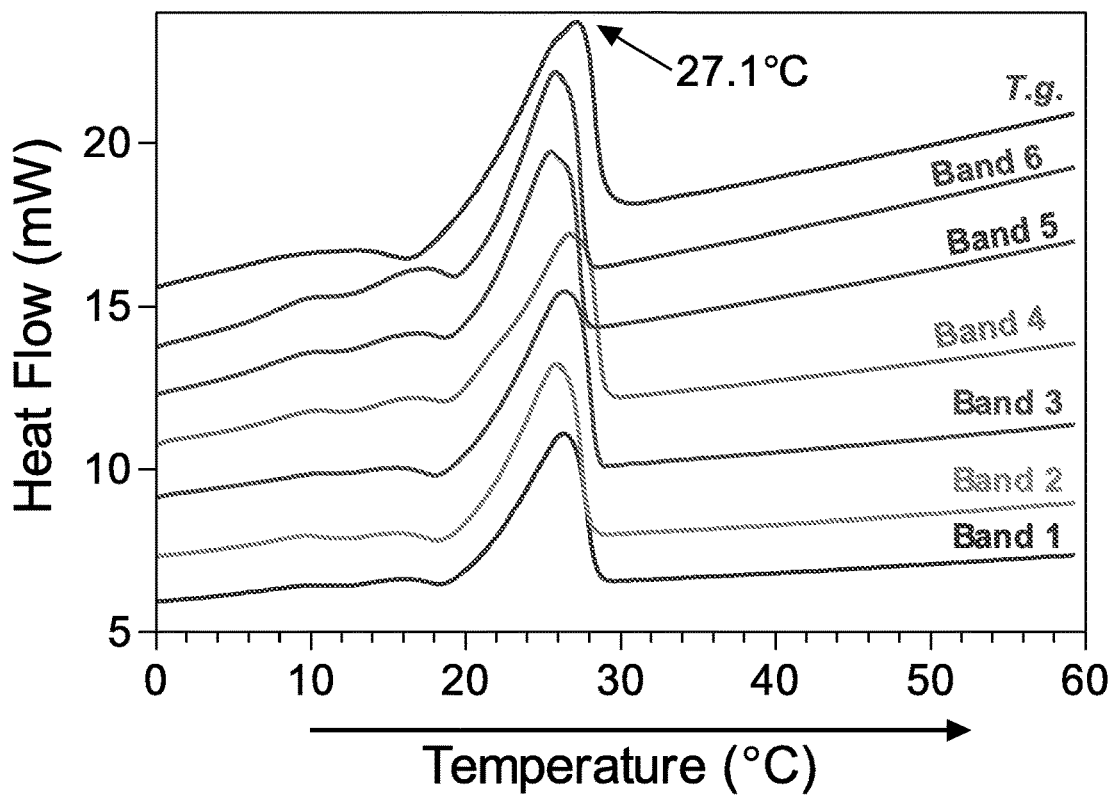
FIGS. 25A and 25B are graphs showing the melting temperatures of cocoa liquor from *T. grandiflorum* (Tg), hybrid seeds obtained from NA-45×MCGS-122, EET400× MCSG-46, and MA-45×MCSG-46 (Bands 1-6), non-hybrid seeds obtained from NA-45×MCGS-122, EET400×MCSG-46, and MA-45×MCSG-46 (Bands 7 and 8), and *T. cacao* (LRWA).
Figure 25B:
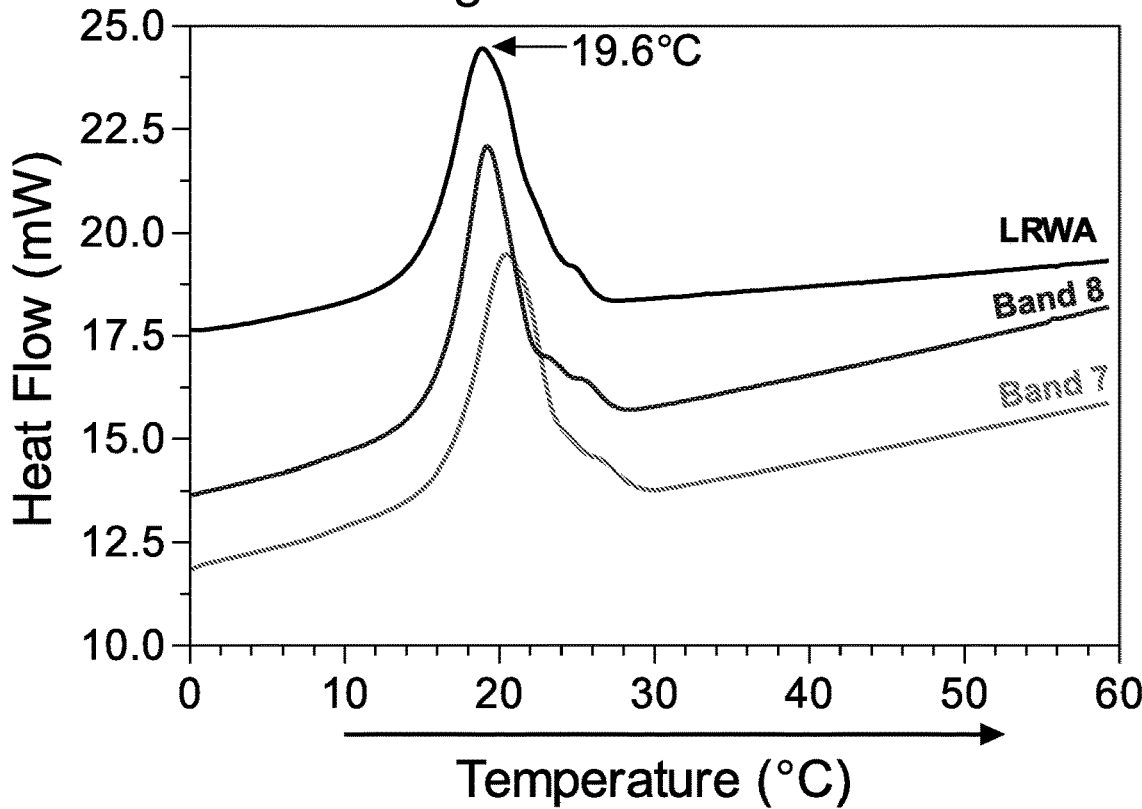
Figure 26A:
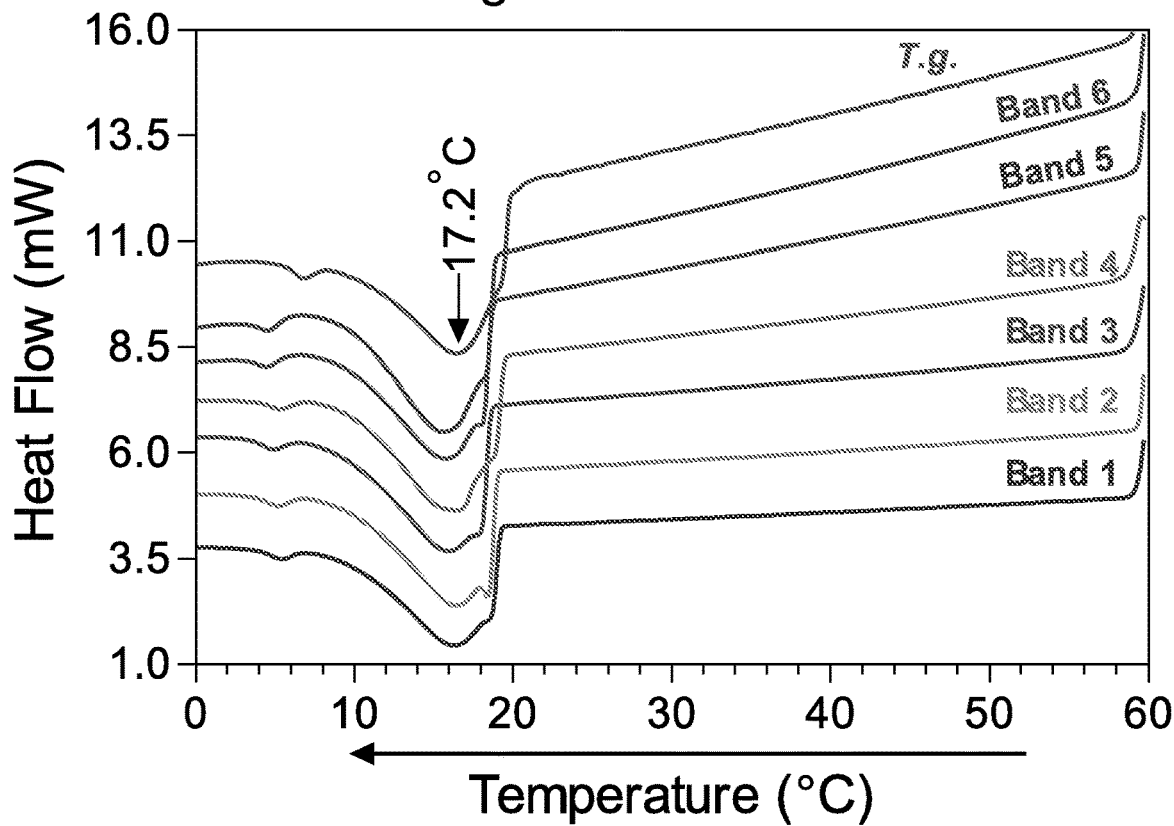
FIGS. 26A and 26B are graphs showing the crystallization temperatures of cocoa liquor from *T. grandiflorum* (Tg), hybrid seeds obtained from NA-45×MCGS-122, EET400× MCSG-46, and MA-45×MCSG-46 (Bands 1-6), non-hybrid seeds obtained from NA-45×MCGS-122, EET400×MCSG-46, and MA-45×MCSG-46 (Bands 7 and 8), and *T. cacao* (LRWA).
Figure 26B:
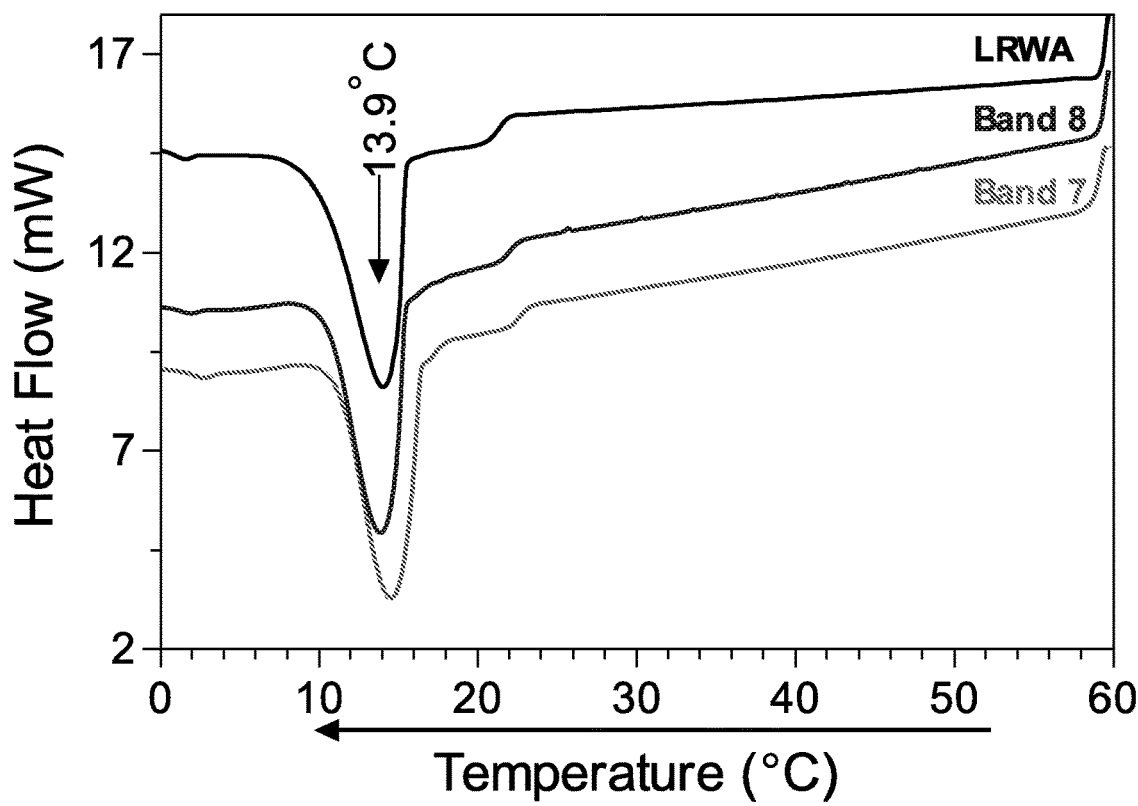
Figure 27:
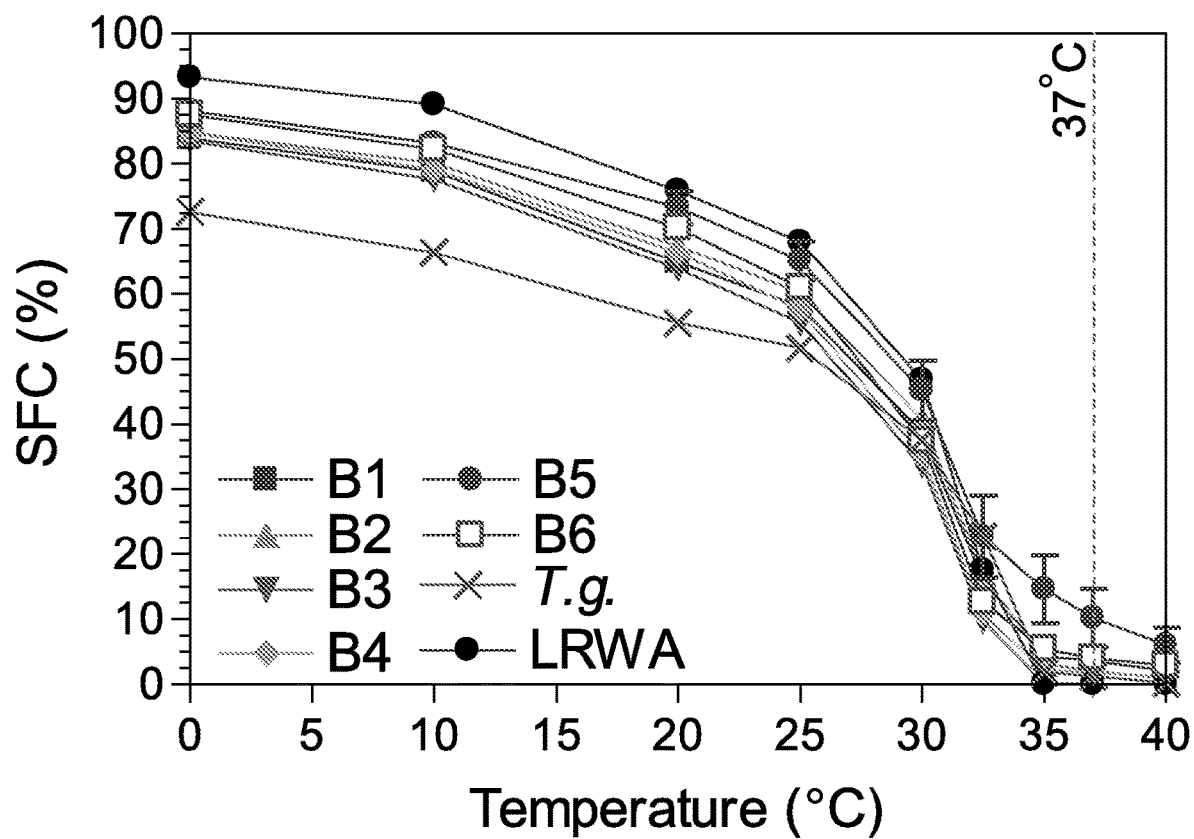
FIG. 27 is a graph showing the melting profile of cocoa liquor from *T. grandiflorum* (Tg), hybrid seeds obtained from NA-45×MCGS-122, EET400×MCSG-46, and MA-45×MCSG-46 (Bands 1-6), and *T. cacao* (LRWA).

The results are shown in FIG. 25 (melting temperature), FIG. 26 (crystallization temperature), and FIG. 27 (melt profiles). The data shows that liquor from seeds of *T. cacao*×*T. grandiflorum* crosses have a higher melting temperature than *T. cacao*, higher crystallization temperature than *T. cacao*, and is suitable for making cocoa products since, for example, the melt profiles are similar to *T. cacao*.

In order to make a 70% chocolate product, for example, 30% sugar is added to the liquor. Methods of making the chocolate or caramel etc. (without cellodextrins) are well known to skilled artisans and can also be found in textbooks such as Chocolate, Cocoa and Confectionery, Bernard W. Minifie Third Edition, which is hereby incorporated by reference.

Example 4

This example shows that a *T. cacao* and *T grandiflorum* hybrid plant can be backcrossed with one of its parents.

Choice of Progenitors

The male parent was selected from one of the hybrid plants described herein based on its low palmitic acid profile, morphological traits and DNA analysis confirming the hybridization between *T. cacao* and *T. grandiflorum*. The female parent used in the backcross was the *T. cacao* parent.

Pollinations

The pollinations were performed manually by covering flowers of the female parent with polyethylene tubes for 24 hours, prior to anthesis. On the day of pollination, the tubes were removed and stigma of the flowers of the female parent were exposed by removing the staminodes. After that, pollen from *Herrania* sp was dipped onto the stigma in order to overcome pollen incompatibility. Next, the pollen from fresh flowers of the hybrid was rubbed onto the stigma of the *T. cacao* parent. Additionally, pollination without pollen from *Herrania* sp. was also performed. In the next step, the pollinated flowers were protected with the same polyethylene tube in order to prevent any unexpected pollination during 24 hours. After this time period, the tube was removed and the success of pollination was checked for 30 days.

Collection of Hybrid Seeds

Around 140 to 160 days after pollination the mature pods were collected and taken to the laboratory, where they were cleaned with bleached water, flamed and then opened under the laminar flow hood. The seeds were then taken out from the pods with sterile forceps and put in sterile Petri dishes. Then, the seed testa was peeled off and one third of the seed, corresponding to the region containing the endosperm, was cut and sent for chemical analysis of fatty acids content. The rest of the seed was then sown in Wood Plant Medium (Lloyd and McCown's, 1981), and placed in a growth room at about 27° C., 70% RH and LED artificial illumination ranging from 90 a 120 $\mu mol \cdot m^{-2} \cdot s^{-1}$.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application.

The embodiments described herein are capable of modification, alteration, and equivalents in form and function, as will occur to those ordinarily skilled in the pertinent arts having the benefit of this disclosure.

REFERENCES

Adamson et al., "HPLC method for the Quantification of Procyanidins in Cocoa and Chocolate Samples and Correlation to Total Anti-oxidant Capacity," J. Agric. Food Chem. 47, 1999, 4184-4188

Addison G. O., Tavares R. M. 1951. Observações sobre as espécies do gênero *Theobroma* que ocorrem na Amazônia. Boletim Técnico do Instituto Agronômico do Norte 25:3-20.

Addison G. O., Tavares R. M. 1952. Hybridization and grafting in species of *Theobroma* which occur in Amazonia. Evolution 6: 380-386.

Bartley B. G. D. 2005. The Genetic diversity of cacao and its utilization. CABI Publishing. 341 pp.

Blauch, J. L. and Stanley, M. T., "Determination of Caffeine and Theobromine in Coffee, Tea and Instant Hot Cocoa Mixes," Journal of Food Science, 48, (1983), pp. 745-747.

Borrone et al., Theor. Appl. Genet. 109 (3), 495-507 (2004).

Campos R. (2005) Experimental Methodology, in Fat Crystal Networks, Editor Alejandro G. Marangoni, Marcel Dekker, USA. pp. 267-348

Carpenter D. R., Hammerstone J. F., Romanczyk L. J. and Aitken W. M. 1994. Lipid Composition of *Herrania* and *Theobroma* Seeds. J. Am. Oil Chem. Soc. 71: 845-851.

Christie, W. W., J. Lipid Res., 23, 1072-1075 (1982).

Christie, W. W., (1989) Gas Chromatogrpahy and Lipids: A Practical Guide, The Oily Press, Dundee.

Ciucanu, I. and Kerek, F., J. Chromatography, 279, 493-506 (1984).

Cuatrecasas, J. 1964. Cacao and its allies: a taxonomic revision of the genus *Theobroma*. Contributions from The United States National Herbarium 35: 379-614.

Figueira A., Pires J. L., Cascardo J. C. M., Cardoso R. D., Nascimento C. S., Lambert S. V. 2000. Cocoa butter quality can be improved by genetic breeding for fatty acid and triacylglycerol composition and hardness. In. Proceedings 12th International Cocoa Research Conference, Salvador, Bahia, Brazil, 17-23 de novembro de 1996. Cocoa Producers' Alliance, Lagos, Nigeria. pp. 399-407.

Gilabert-Escrivá M. V., Gonçalves L. A. G., Figueira A. Silva C. R. S. 2002. Fatty acid and triacylglycerol composition and thermal behavior of fats from seeds of Brazilian Amazonian *Theobroma* species. Journal of the Science of Food and Agriculture 82:1425-1431.

Gunstone F. D., Harwood J. L., Padley F. B. 1994. The lipid handbook. Chapman and Hall. London.

Kelm et al., "HPLC separation and purification of cacao (*Theobroma cacao* L.) procyanidins according to degree of polymerization using a diol stationary phase," J Agric. Food Chem. 54, 2006, 1571

Kuhn D. N., Figueira A. Lopes, U. Motamayor J. C., Meerow A. W. Cariaga K. & Freeman B. & Livingstone D. S Schnell R. J. 2010. Evaluating *Theobroma grandiflorum* for comparative genomic studies with *Theobroma cacao*. Tree Genetics & Genomes. 6:783-792

Kuhn et al., Tree Genetics & Genomes 8, 97-111 (2012).

Livingstone et al., Mol Breeding 27:93-106 (2011).

Martinson V. A. 1966. Hybridisation of cacao and *Theobroma grandiflora*. Journal of Heredity 57: 134-136.

Posnette A. F. 1945. Interspecific pollination in *Theobroma*. Tropical Agriculture 22: 188-190.

Pugh et al., Theor. Appl. Genet. 108 (6), 1151-1161 (2004).

Silva C. R. S., Venturieri G. A., Figueira A. 2004. Description of Amazonian *Theobroma* L. collections, species identification, and characterization of interspecific hybrids. Acta Botanica Brasilis 18: 333-341.

What is claimed is:

1. A method for producing a hybrid plant or seed of *Theobroma cacao* and *Theobroma grandiflorum*, comprising:
(a) crossing a variety of *Theobroma cacao* and a variety of *Theobroma grandiflorum* to obtain progeny seeds therefrom;
(b) analyzing at least a portion of the progeny seeds for the presence of a single nucleotide polymorphism (SNP) marker indicative of a *Theobroma cacao* and *Theobroma grandiflorum* hybrid, wherein said SNP marker is w17s189(T/C), e0050s274(CAT), CIR211s1036(T/A), c3s595(C/A), w3 s41(G/T), w8s131(T/C), w3s558 (A/G), or any combination thereof; and
(c) selecting one or more hybrid seeds from the progeny seeds analyzed in step (b) to produce the hybrid plant or seed.

2. The method of claim 1, further comprising growing seed that is selected in step (c).

3. The method of claim 1, wherein at least one of the following applies: (i) step (a) comprises applying pollen of *Theobroma grandiflorum* to female parts of *Theobroma cacao*; (ii) step (a) further comprises harvesting mature pods between 140 and 160 days after pollination, and seeds are removed therefrom; and/or (iii) step (c) comprises removing a sample of cotyledon from said seeds and analyzing the chemical and/or genetic composition of said seeds.

4. The method of claim 3, where step (b) further comprises removing ⅓ of said cotyledon.

5. The method of claim 3, further comprising sowing said hybrid seeds in a growth medium and incubating said hybrid seeds in a growth room until hybrid plantlets have been formed and optionally thereafter.

6. The method of claim 5, wherein the growth medium is a woody plant medium.

7. The method of claim 5, further comprising incubating said hybrid seeds at a temperature of from 27-30° C. and at 70% relative humidity.

8. The method of claim 5, wherein said hybrid seeds are incubated for 10-15 days.

9. The method of claim 5, further comprising holding said hybrid plantlets in a humid chamber with at least 90% humidity.

10. The method of claim 5, further comprising transferring said hybrid plantlets to a suitable substrate comprising peat moss, coconut powder, perlite or mixtures thereof.

11. The method of claim 5, further comprising grafting said hybrid plantlets onto a *Theobroma cacao* or *Theobroma grandiflorum* plant.

12. The method of claim 1, wherein step (b) further comprises analyzing at least a portion of the progeny seeds for the presence of tetramethyluric acid, and wherein the one or more hybrid seeds are one or more progeny seeds that comprise tetramethyluric acid.

13. The method of claim 1, wherein the one or more hybrid seeds are one or more progeny seeds that exhibit a single nucleotide polymorphism (SNP) marker indicative of a *Theobroma cacao* and *Theobroma grandiflorum* hybrid, wherein the SNP marker is w17s189(T/C), e0050s274(C/T), CIR211s1036(T/A), c3s595(C/A), w3s41(G/T), w8s131(T/C), or w3s558(A/G).

14. The method of claim 1, wherein step (b) further comprises one or more of the following characteristics for which at least a portion of the progeny seeds are analyzed: (i) decreased palmitic acid as compared to *Theobroma cacao*; (ii) decreased theobromine compared to *Theobroma cacao*; and (iii) the presence of tetramethyluric acid.

15. The method of claim 14, wherein the one or more hybrid seeds are one or more progeny seeds that further exhibit one or more of the following characteristics: (i) decreased palmitic acid as compared to *Theobroma cacao*; (ii) decreased theobromine compared to *Theobroma cacao*; and the presence of tetramethyluric acid.

* * * * *

UNITED STATES PATENT AND TRADEMARK OFFICE
CERTIFICATE OF CORRECTION

PATENT NO. : 10,791,689 B2
APPLICATION NO. : 15/542381
DATED : October 6, 2020
INVENTOR(S) : Jean-Philippe Marelli et al.

Page 1 of 1

It is certified that error appears in the above-identified patent and that said Letters Patent is hereby corrected as shown below:

In the Claims

At Column 39, Claim number 1, Line number 12:
Delete "e0050s274(CAT),"
Insert --e0050s274(C/T),--

At Column 40, Claim number 15, Line number 35:
Delete "and the presence of tetramethyluric acid."
Insert --and (iii) the presence of tetramethyluric acid.--

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 36

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgattacact gttacaccaa ctttagacg                                      29

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acgtgtaaag aaaggaggaa aacttt                                         26

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcttgctgag atatc                                                     15

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tctcttgccg agatat                                                    16

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctcaggttcc aaccattgat ttaa                                           24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccgagatccc atggttaaca a                                              21

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aagctgccac ggagt                                                     15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aagctgccat ggagt                                                     15

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aacttgtcag ctgtctctct ttcttg                                         26

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cagaactgtg catgcttgaa gc                                             22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctaaatgaat catccaaaga                                                20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaatgaatca cccaaaga                                                  18

```
<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaaggcaatc cttacccaag gt                                             22

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aagaatgaac cactttgcag tagatagt                                       28

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atgcccctgg ttgt                                                      14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atgcccctgt ttgt                                                      14

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gttgttgttc tgttcaattc gtatga                                         26

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atcaggaatg ctccaaaata atcaa                                          25
```

```
<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgactacctt ttatgtgatc t                                              21

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgactgcctt ttatgtgat                                                 19

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gccctgtcaa aagaaggta ctg                                             23

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttactgttgc tttccatttt ctaagtg                                        27

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ttctgaggta tcattccca                                                 19

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ttctgaggca tcattcc                                                   17

<210> SEQ ID NO 25
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cacttagaaa atggaaagca acagt                                           25

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
acctagagcc agatgatgaa ttgtatt                                         27

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ttcctgagac ttgtacttga                                                 20

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ttcccgagac ttgtactt                                                   18

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgctggtggc aagaagtatt atattag                                         27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cagatcctca ttcaatacct gtatcaa                                         27

<210> SEQ ID NO 31
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctctgcatca ttggt                                                     15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ctctgcctca ttggt                                                     15

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
accttaattt tatgggaaac gaggt                                          25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccaaacaaaa tcttaatgca ctgtg                                          25

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aatctgtgct gactgat                                                   17

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
caatcagtgc tgactg                                                    16
```